United States Patent
Nishimune et al.

(10) Patent No.: US 11,286,462 B2
(45) Date of Patent: Mar. 29, 2022

(54) MATERIALS AND METHODS FOR GENERATING THERAPEUTIC MESENCHYMAL STEM CELLS

(71) Applicant: University of Kansas, Lawrence, KS (US)

(72) Inventors: Hiroshi Nishimune, Kansas City, MO (US); Richard Barohn, Kansas City, MO (US); Buddhadeb Dawn, Mission Hills, KS (US); Yomna Badawi, Leawood, KS (US); James W. Mitchell, Overland Park, KS (US); Rupal Soder, Prairie Village, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 16/647,345

(22) PCT Filed: Sep. 14, 2018

(86) PCT No.: PCT/US2018/050989
§ 371 (c)(1),
(2) Date: Mar. 13, 2020

(87) PCT Pub. No.: WO2019/055729
PCT Pub. Date: Mar. 21, 2019

(65) Prior Publication Data
US 2020/0399610 A1   Dec. 24, 2020

Related U.S. Application Data

(60) Provisional application No. 62/558,527, filed on Sep. 14, 2017.

(51) Int. Cl.
*C12N 5/0775* (2010.01)
*A61K 35/51* (2015.01)

(52) U.S. Cl.
CPC ............ *C12N 5/0668* (2013.01); *A61K 35/51* (2013.01); *C12N 2500/32* (2013.01); *C12N 2501/10* (2013.01); *C12N 2501/105* (2013.01); *C12N 2501/115* (2013.01); *C12N 2501/13* (2013.01); *C12N 2501/135* (2013.01); *C12N 2501/165* (2013.01); *C12N 2533/52* (2013.01)

(58) Field of Classification Search
CPC .............. C12N 5/0668; C12N 2501/13; C12N 2501/165; C12N 2501/10; C12N 2501/115; C12N 2501/135; C12N 2501/105; C12N 2500/32; A61K 35/51
See application file for complete search history.

(56) References Cited

FOREIGN PATENT DOCUMENTS

WO    2014/024183 A1   2/2014

OTHER PUBLICATIONS

Huang et al., Effects of insulin-like growth factor-1 on the properties of mesenchymal stem cells in vitro. J Zhejiang Univ Sci B, vol. 13, No. 1 (Jan. 2012) pp. 20-23. (Year: 2012).*
Frausin et al., Wharton's jelly derived mesenchymal stromal cells: Biological properties, induction of neuronal phenotype and current applications in neurodegeneration research. Acta Histochemica, vol. 117, No. 4-5 (May-Jun. 2015) pp. 329-338. (Year: 2015).*
Subramanian et al., Comparative characterization of cells from the various compartments of the human umbilical cord shows that the Wharton's jelly compartment provides the best source of clinically utilizable mesenchymal stem cells. PLoS ONE, vol. 10 (Jun. 10, 2015) No. 6, e0127992. (Year: 2015).*
Balice-Gordon et al., "Long-term synapse loss induced by focal blockade of postsynaptic receptors," Nature, 1994, 372 (6506):519-524.
Billings et al., "ELKS1 and Ca2+ channel subunit β4 interact and colocalize at cerebellar synapses," Neuroreport, 2012, 23(1):49-54.
Browne et al., "Recent progress towards an effective treatment of amyotrophic lateral sclerosis using the SOD1 mouse model in a preclinical setting," Eur J Med Chem, 2016, 121:918-925.
Buffelli et al., "Genetic evidence that relative synaptic efficacy biases the outcome of synaptic competition," Nature, 2003, 424(6947):430-434.
Chen et al., "Active zone density is conserved during synaptic growth but impaired in aged mice," J Comp Neurol, 2012, 520(2):434-452.
Chen et al., "Calcium channels link the muscle-derived synapse organizer laminin β2 to Bassoon and CAST/Erc2 to organize presynaptic active zones," J Neurosci, 2011, 31(2):512-525.
Clarke et al., "Presynaptic Active Zone Density during Development and Synaptic Plasticity," Front Mol Neurosci, 2012, 5:12.
Clinical Trials NCT02881476, "Therapeutic Treatment of Amyotrophic Lateral Sclerosis (UwmWjmscAIs)," 2016.
Dadon-Nachum et al., "The "dying-back" phenomenon of motor neurons in ALS," J Mol Neurosci, 2011, 43(3):470-477.
Ellis et al., "Volumetric analysis reveals corticospinal tract degeneration and extramotor involvement in ALS," Neurology, 2001, 57(9):1571-1578.
Fischer et al., "Amyotrophic lateral sclerosis is a distal axonopathy: evidence in mice and man," Exp Neurol, 2004, 185 (2):232-240.
Frausin et al., "Wharton's jelly derived mesenchymal stromal cells: Biological properties, induction of neuronal phenotype and current applications in neurodegeneration research," Acta Histochemica, 2015,117(4-5):329-338.

(Continued)

*Primary Examiner* — Kara D Johnson
(74) *Attorney, Agent, or Firm* — Michael Best & Friedrich LLP

(57) ABSTRACT

Embodiments of the present disclosure relate generally to the production of therapeutic mesenchymal stem cells (MSCs). More particularly, the present disclosure relates to the use of cell culture compositions and methods for generating MSCs that secrete neurotrophic factors and synaptic organizing agents for the treatment of neurodegenerative diseases such as Amyotrophic Lateral Sclerosis (ALS). As such, the present disclosure addresses the need for establishing a reliable source of therapeutic stem cells useful for the treatment of neurodegenerative diseases.

12 Claims, 33 Drawing Sheets

(56) References Cited

OTHER PUBLICATIONS

Frey et al., "Early and selective loss of neuromuscular synapse subtypes with low sprouting competence in motoneuron diseases," J Neurosci, 2000, 20(7):2534-2542.
Gould et al., "Complete dissociation of motor neuron death from motor dysfunction by Bax deletion in a mouse model of ALS," J Neurosci, 2006, 26(34):8774-8786.
Gurney et al., "Motor neuron degeneration in mice that express a human Cu,Zn superoxide dismutase mutation," Science, 1994, 264, 1772-1775.
Ince et al., "Amyotrophic lateral sclerosis associated with genetic abnormalities in the gene encoding Cu/Zn superoxide dismutase: molecular pathology of five new cases, and comparison with previous reports and 73 sporadic cases of ALS," J Neuropathol Exp Neurol, 1998, 57(10):895-904.
Kennel et al., "Neuromuscular function impairment is not caused by motor neurone loss in FALS mice: an electromyographic study," Neuroreport, 1996, 7(8):1427-1431.
Maselli et al., "Mutations in LAMB2 causing a severe form of synaptic congenital myasthenic syndrome," J Med Genet, 2009, 46(3):203-208.
Nishimune et al., "A synaptic laminin-calcium channel interaction organizes active zones in motor nerve terminals," Nature, 2004, 432(7017):580-587.
Nishimune et al., "Active zone protein Bassoon co-localizes with presynaptic calcium channel, modifies channel function, and recovers from aging related loss by exercise," PLoS One, 2012, 7(6):e38029.
Nishimune et al., "Reg-2 is a motoneuron neurotrophic factor and a signalling intermediate in the CNTF survival pathway," Nat Cell Biol, 2000, 2(12):906-914.
Nishimune, "Active zones of mammalian neuromuscular junctions: formation, density, and aging," Ann N Y Acad Sci, 2012, 1274:24-32.
Noakes et al., "Aberrant differentiation of neuromuscular junctions in mice lacking s-laminin/laminin β2," Nature, 1995, 374(6519):258-262.

Pun et al., "Selective vulnerability and pruning of phasic motoneuron axons in motoneuron disease alleviated by CNTF," Nat Neurosci, 2006, 9(3):408-419.
Schaefer et al., "A compensatory subpopulation of motor neurons in a mouse model of amyotrophic lateral sclerosis," J Comp Neurol, 2005,490(3):209-219.
Schiffer et al., "Ubiquitinated dystrophic neurites suggest corticospinal derangement in patients with amyotrophic lateral sclerosis," Neurosci Lett, 1994,180(1):21-24.
Zenker et al., "Human laminin β2 deficiency causes congenital nephrosis with mesangial sclerosis and distinct eye abnormalities," Human molecular genetics, 2004, 13(21):2625-2632.
International Search Report and Written Opinion, PCT/US2018/050989, dated Jan. 2, 2019.
(Noro, A et al.) Laminin Production and Basement Membrane Deposition by Mesenchymal Stem Cells upon Adipogenic Differentiation. Journal of Histochemistry and Cytochemistry. Oct. 2013, Epub Jul. 30, 2013, vol. 61, No. 10, pp. 719-730; abstract; Figure 1; DOI: 10.1369/0022155413502055.
(Huang, Yet al.) Effects of insulin-like growth factor-1 on the properties of mesenchymal stem cells in vitro. Journal of Zhejiang University Science B. Jan. 2012, vol. 13, No. 1, pp. 20-28; abstract; DOI: 10.1631/jzus.B1100117.
(Koch, H et al.) Insulin-like Growth Factor-I Induces Early Osteoblast Gene Expression in Human Mesenchymal Stem Cells. Stem Cells in Development. Dec. 2005, Epub Jan. 24, 2006, vol. 14, No. 6, pp. 621-631 abstract; p. 622, 2nd column, 1st paragraph; DOI: 10.1089/scd.2005.14.621.
(Tao, Yet al.) TGF-b3 and IGF-1 synergy ameliorates nucleus pulposus mesenchymal stem cell differentiation towards the nucleus pulposus cell type through MAPK/ERK signaling. Growth Factors. Oct. 2, 2015, vol. 33, No. 5-6, pp. 326-336; abstract; DOI: 10.3109/08977194.2015.1088532.
(Youssef, A et al.) The Roles of Insulin-Like Growth Factors in Mesenchymal Stem Cell Niche. Stem Cells International. Feb. 16, 2017, vol. 2017; p. 5, 1st column, 1st paragraph; p. 5, 2nd column, 3rd paragraph; DOI: 10.1155/2017/9453108.

* cited by examiner a = Passage 1 remaining WJMSCs are frozen in 5% HSA/10% DMSO/Plasmalyte a A in LN2 vapor at $2.5 \times 10^6$ cells per vial.

| Normalized counts (cpm) | | | Raw counts | | |
|---|---|---|---|---|---|
| D0002 | D0003 | E0007 | D0002 | D0003 | E0007 |
| 486.6 | 313.5 | 508.4 | 10764 | 10115.01 | 10918.99 |

FIG. 14

MATERIALS AND METHODS FOR GENERATING THERAPEUTIC MESENCHYMAL STEM CELLS

CROSS-REFERENCE TO RELATED APPLICATION

This patent application is the U.S. national stage entry, under 35 U.S.C. X371, of International Application Number PCT/US2018/050989, filed Sep. 14, 2018, which claims the benefit of U.S. Provisional Application No. 62/558,527, filed Sep. 14, 2017, the entire contents of each of which are hereby incorporated by reference.

GOVERNMENT FUNDING

This invention was made with government support under grant number R01 NS078214 awarded by the National Institutes of Health. The government has certain rights in the invention.

FIELD

Embodiments of the present disclosure relate generally to the production of therapeutic mesenchymal stem cells (MSCs). More particularly, the present disclosure relates to the use of cell culture compositions and methods for generating MSCs that secrete neurotrophic factors and synaptic organizing agents for the treatment of neurodegenerative diseases such as Amyotrophic Lateral Sclerosis (ALS).

BACKGROUND

Amyotrophic lateral sclerosis (ALS) is one of the progressive neurodegenerative disorders, affecting upper and lower motor neurons in the cerebral cortex, brainstem and spinal cord. Hence, the signs of damage motor neurons are both at the peripheral (e.g., atrophy), and central (e.g., spasticity) level. There is no effective treatment for ALS and the majority of patients die within five years after diagnosis, usually due to the respiratory failure. Numerous studies on murine models revealed that mesenchymal stem cells (MSCs) successfully improve the clinical and pathological features of ALS patients.

ALS patients and animal models show dying-back neuropathy in neuromuscular junctions (NMJs) and the corticospinal tract. Dying-back neuropathy in ALS is characterized by a loss of active zones. Active zones are essential for synaptic transmission as synaptic vesicle accumulation and release sites at presynaptic terminals. It has recently been shown that active zone loss causes NMJ denervation and dying-back neuropathy in mice. In support of this, weaker axons are destabilized and pruned from NMJs during the synapse elimination period or by focal neurotransmission blockade in adult mice. In addition, NMJ denervation is observed in humans and mice that exhibit active zone loss arising from gene mutations or aging. Therefore, there is a need to establish materials and methods for facilitating the production of a reliable source of therapeutic stem cells useful for the treatment of neurodegenerative diseases.

SUMMARY

Embodiments of the present disclosure provide an isolated non-genetically modified human cell activated ex vivo from a mesenchymal stem cell (MSC) under conditions such that the isolated non-genetically modified human cell secretes laminin β2 at a level that is greater than the basal secretion level of laminin β2 by the MSC. In some embodiments, the isolated non-genetically modified human cell further secretes one or more of glial cell-derived neurotrophic factor (GDNF), brain-derived neurotrophic factor (BDNF), and vascular endothelial growth factor (VEGF) at a level that is greater than the basal secretion level of GDNF, BDNF, or VEGF by the MSC. In accordance with these embodiments, the isolated human cell can ameliorate denervation at a neuromuscular junction caused by Amyotrophic Lateral Sclerosis (ALS).

Embodiments of the present disclosure also provide a method for producing a cell from an MSC, such that the cell secretes laminin β2 at a level that is greater than the basal secretion level of laminin β2 by the MSC. In accordance with these embodiments, the method can involve exposing the MSC to a cell culture composition comprising cell culture media and Insulin-like growth factor 1 (IGF-1).

Other aspects of the invention will become apparent by consideration of the detailed description and accompanying drawings.

BRIEF DESCRIPTION OF THE DRAWINGS

FIG. 14 is a chart showing cd140b expression in MSCs derived from three different donors (D0002, D0003, E0007).

DETAILED DESCRIPTION

1. Definitions

Figure 1A:
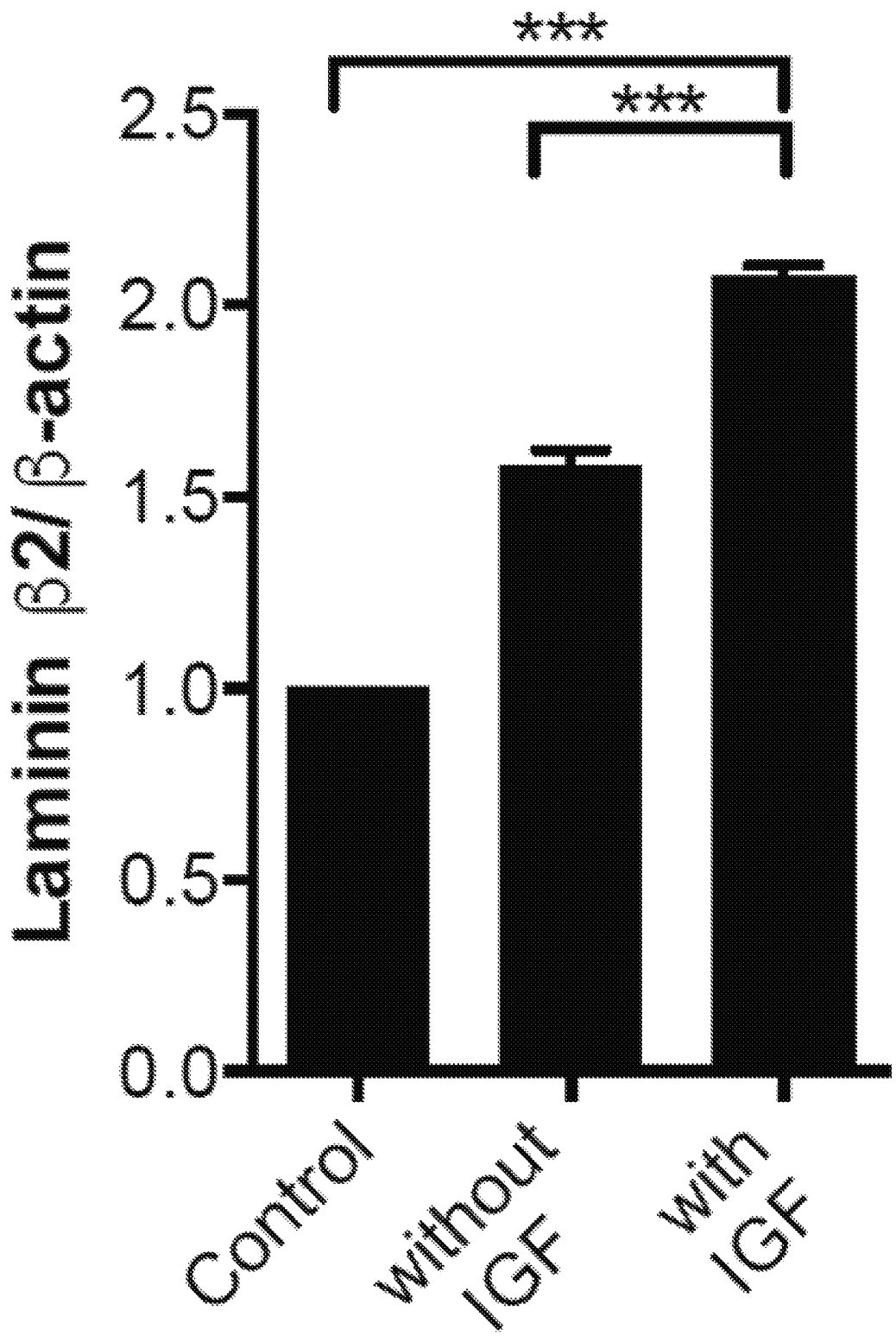
FIGS. 1A-1B are representative graphs depicting the effects of IGF-1 on the culture medium based stimulation of laminin β2 protein secretion (FIG. 1A), and the effects of laminin β2 protein on NMJ denervation rate of SOD1$^{G93A}$ mice (FIG. 1B).

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "activated" or "stimulated" when used interchangeably herein in reference to hMSCs refer to hMSCs that have been exposed to conditions such that the hMSCs secrete laminin β2 at a level that is greater than the basal secretion level of laminin β2 by the hMSCs.

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc.) and a human). In some aspects, the subject is a human.

The terms "treat," "treated," or "treating," as used herein, refer to a therapeutic method wherein the object is to slow down (lessen) an undesired physiological condition, disorder or disease, or to obtain beneficial or desired clinical results. In some aspects of the present disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment.

2. Stimulated MSCs and Methods for Generating the Same

Before any embodiments of the present disclosure are explained in detail, it is to be understood that the present disclosure is not limited in its application to the details of construction and the arrangement of components set forth in the following description or illustrated in the accompanying drawings. The present disclosure is capable of other embodiments and of being practiced or of being carried out in various ways.

Embodiments of the present disclosure relate generally to the production of therapeutic mesenchymal stem cells (MSCs). More particularly, the present disclosure relates to the use of cell culture compositions and methods for generating MSCs that secrete neurotrophic factors and synaptic organizing agents for the treatment of neurodegenerative diseases such as Amyotrophic Lateral Sclerosis (ALS).

The organization of the NMJ active zones via interactions between a synapse organizer laminin β2, the specific receptor for the organizer, and active zone specific proteins has previously been shown. Using this molecular mechanism as the basis for further investigation, the present disclosure demonstrates that NMJs in SOD1$^{G93A}$ mice can be maintained by overexpressing laminin β2 in muscles (see, e.g., FIG. 1B). SOD1$^{G93A}$ mice express human superoxide dismutase 1 with the G93A mutation identified in human patients. These mice replicate human disease symptoms and are one of the most commonly used ALS model animals available.

The present disclosure has identified that NMJ denervation and dying back neuropathy occur in SOD1$^{G93A}$ mice due to degeneration of presynaptic specialization at NMJs, namely the presynaptic active zones. As described herein, degeneration of active zones was due to reduction of synapse organizer laminin β2 and the reduction of active zone number cause denervation of NMJs. Additionally, NMJ denervation was ameliorated in double transgenic SOD1$^{G93A}$ mice and mice overexpressing laminin β2 in skeletal muscles (see, e.g., FIG. 1B), suggesting that NMJ denervation in SOD1$^{G93A}$ mice can be ameliorated by intramuscular injection of human mesenchymal stem cells (hMSCs) expressing laminin β2.

Human mesenchymal stem cell data. Embodiments of the present disclosure used human mesenchymal stem cells (hMSCs) derived from umbilical cord to deliver laminin 12 and neurotrophic factors to NMJs for ameliorating NMJ denervation in ALS model mice SOD1$^{G93A}$ mice. MSCs may be positive for the biomarker CD140b. MSCs may be differentiated from other umbilical cord stem cells based upon the presence of the biomarker CD140b. hMSCs were produced at the Midwest Stem Cell Therapy Center of University of Kansas Medical Center. In accordance with these embodiments, cell culture conditions were identified that increased the secretion of laminin β2 from hMSCs. hMSCs were grown in Dulbecco's Modified Eagle Medium/Nutrient Mixture F-12 (DMEM/F12) containing 10% FBS to 70% confluency in 10 cm dish. The hMSCs were stimulated for 72 hours in DMEM/F12 media (containing 2.5 mM L-glutamine) supplemented with human basic fibroblast growth factor (20 ng/ml), human Epidermal growth factor (20 ng/ml), N2 supplement (10 µl/ml). The hMSCs were stimulated additionally for 72 hours in DMEM/F12 media (containing 2.5 mM L-glutamine) supplemented with 0.5 mM 3-isobutyl-1-methylxanthine (IBMX), 1 mM dibutyryl Cyclic adenosine monophosphate (AMP), human basic fibroblast growth factor (20 ng/ml), heregulin β1 (50 ng/ml), human platelet-derived growth factor (5 ng/ml), and human insulin-like growth factor 1 (20 ng/ml). After stimulation in these culture medium, hMSCs increased significantly the secretion of synapse organizer (laminin β2) and neurotrophic factors (Brain-derived neurotrophic factor (BDNF), Glia cell-derived neurotrophic factor (GDNF), and Vascular endothelial growth factor (VEGF)) (FIG. 1A, FIGS. 2A-C). The stimulated hMSCs were analyzed using BD Human Mesenchymal Stem Cell Analysis Kit (Manufacturer: BD 562245). The stimulated hMSCs maintained CD-73, CD-90, and CD-105 expression, but did not express the following negative-lineage markers: CD11b, CD19, CD34, CD45, and HLA-DR. These results demonstrate that hMSCs maintained a multipotent state when cultured according to these conditions.

Figure 3A:
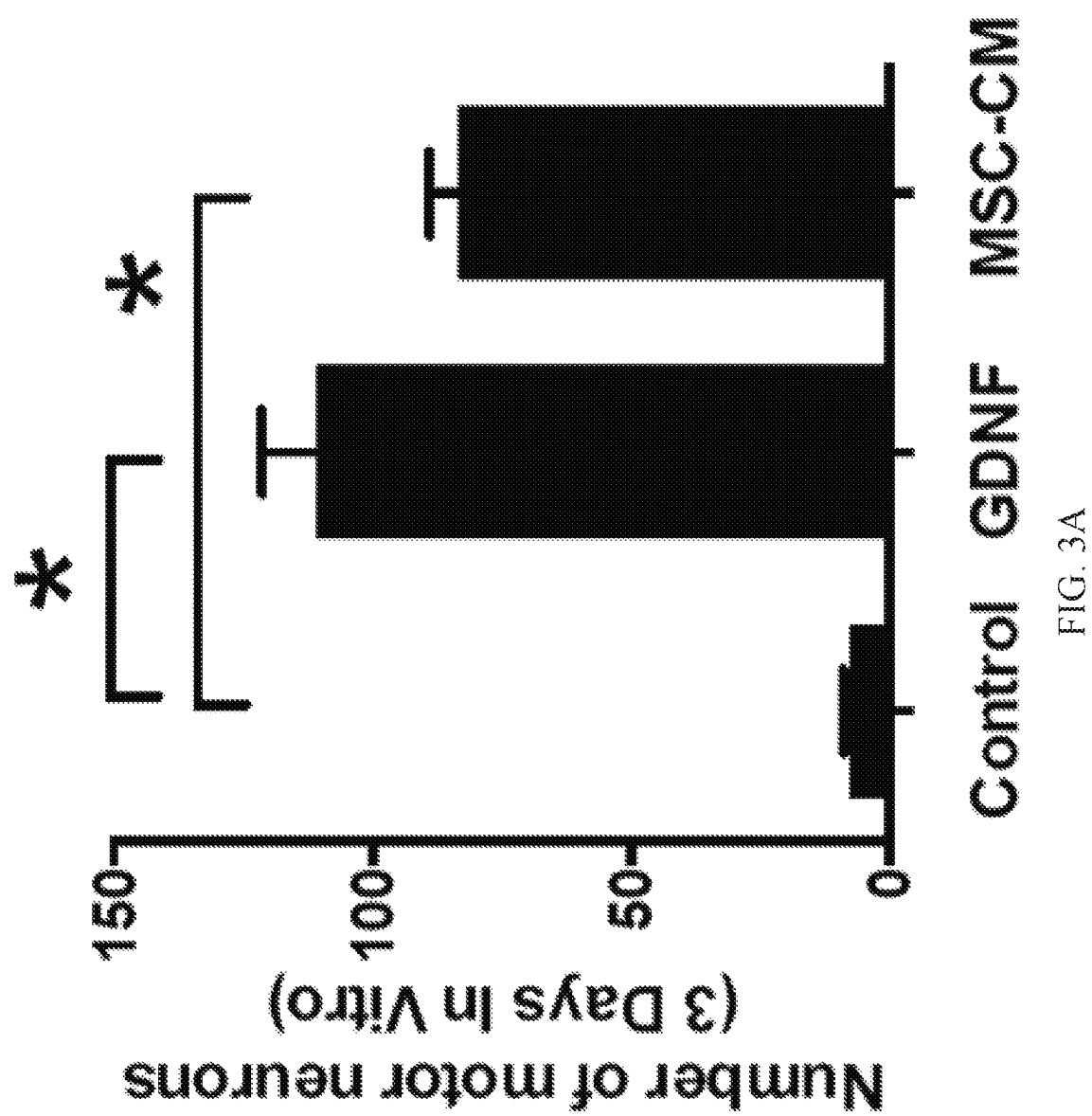
FIGS. 3A and 3B are graphs and images relating to secreted proteins from human MSCs that enhanced the survival of spinal cord motor neurons.
Figure 3B:
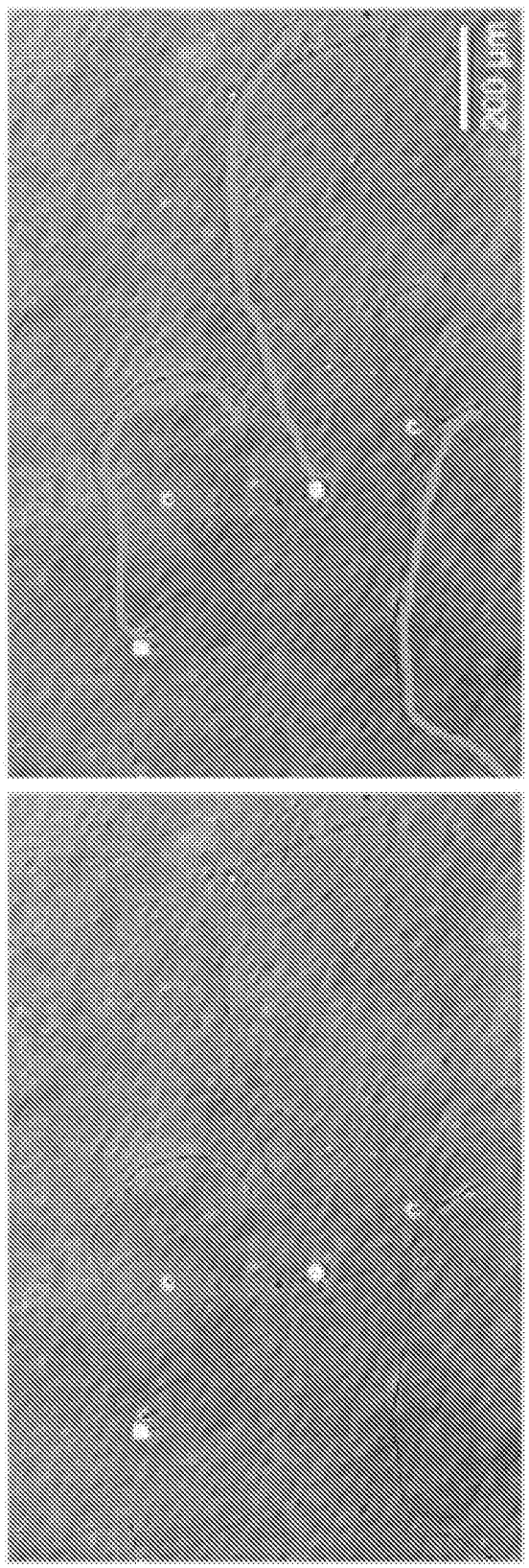

The biological activity of the factors secreted from hMSCs was tested using motor neurons purified from wild-type mouse spinal cord using published protocol. The survival of cultured motor neurons depends on exogenously supplied neurotrophic factors, and the primary motor neurons will not survive without trophic factor support. For a positive control, motor neurons were cultured in recombinant human GDNF added at 0.1 ng/ml. hMSCs conditioned medium increased significantly the survival rate of cultured primary motor neurons, which was similar to the survival rate of positive control GDNF (FIGS. 3A-3B). These results indicate that the stimulated hMSCs secrete biologically active neurotrophic factors that maintain the survival of spinal motor neurons.

3. Treatment of Disease

Figure 7A:
FIGS. 7A, 7B, 7C and 7D are images of the results of vivo injection of human MSCs into an ALS mice model.
Figure 7B:
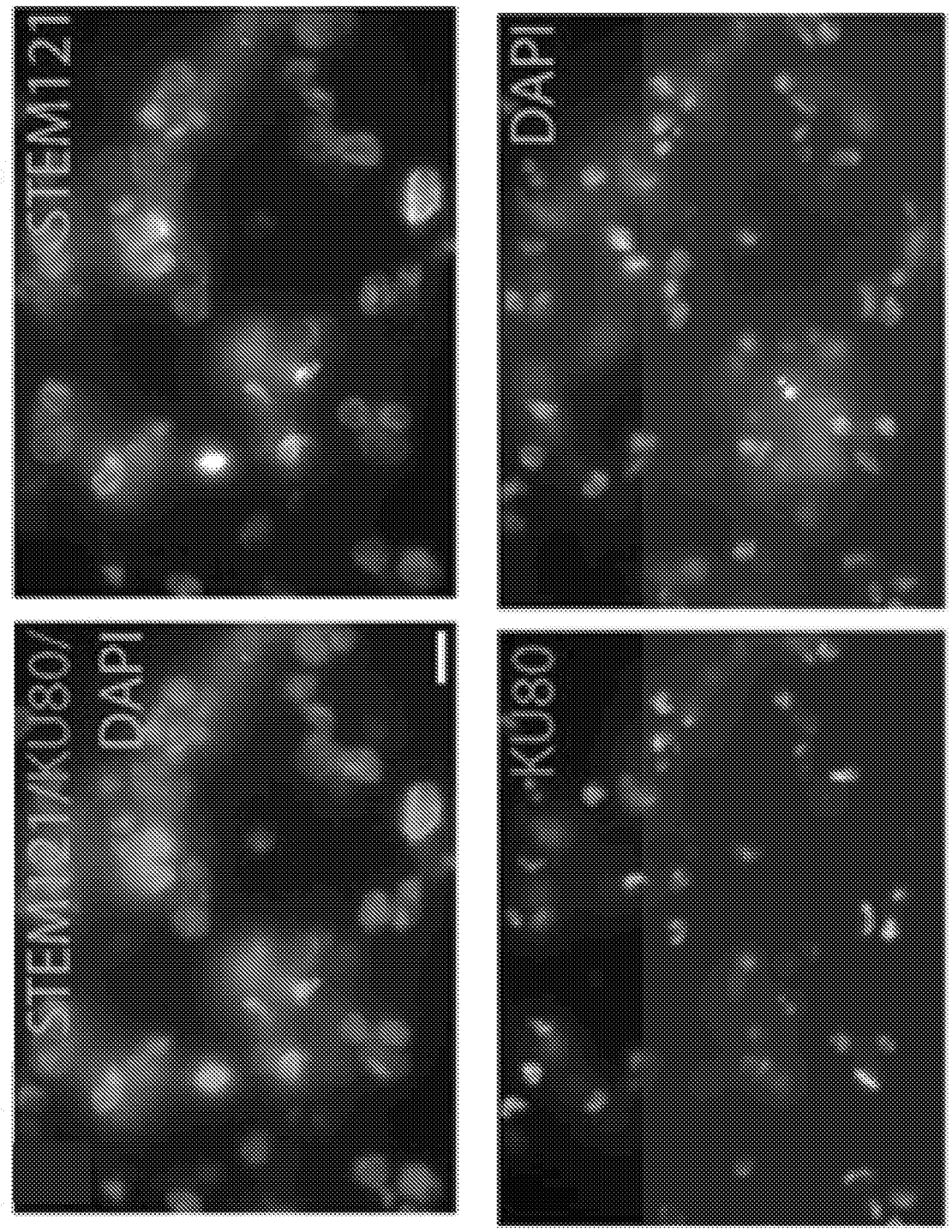
Figure 7C:
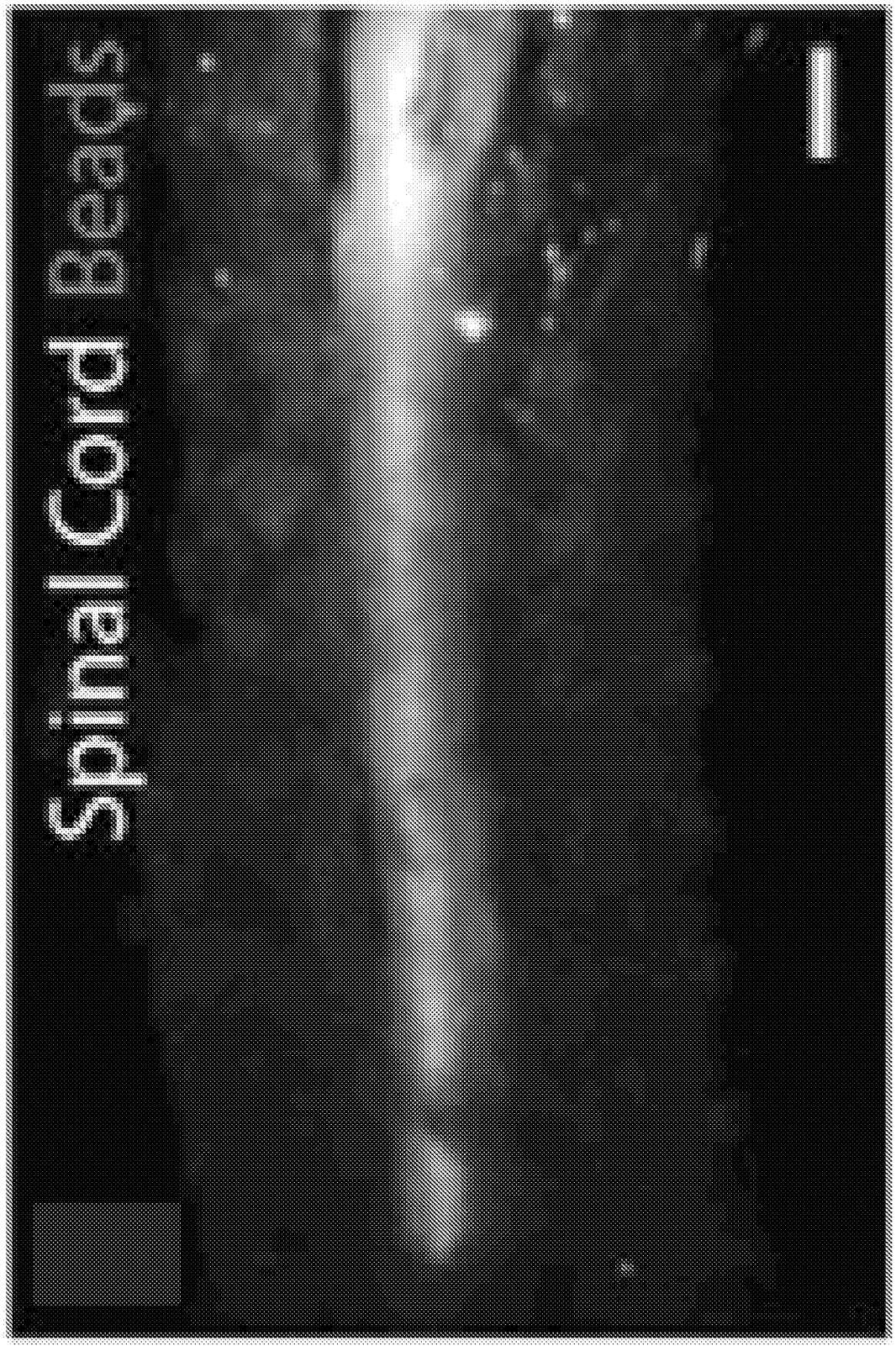
Figure 7D:
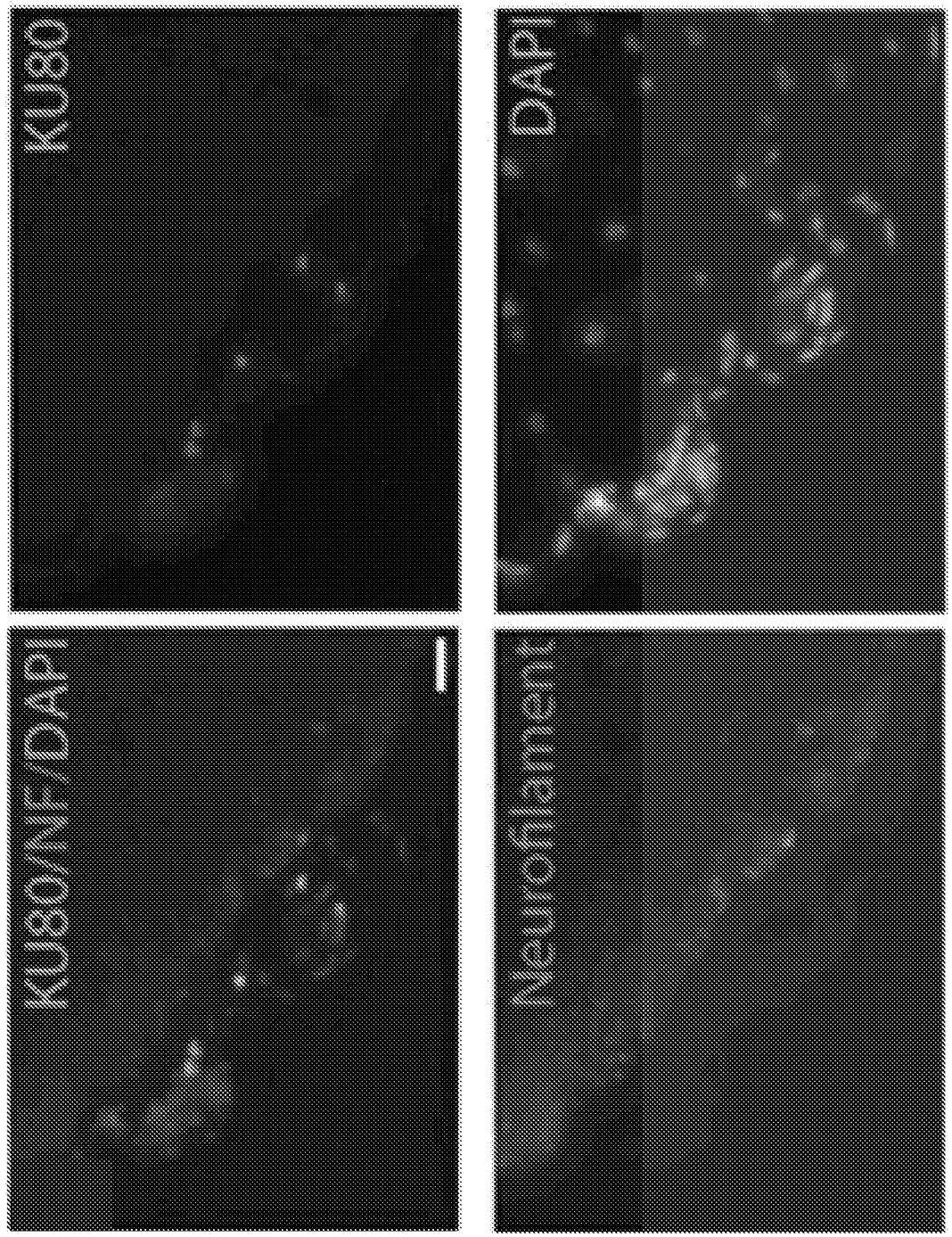

The stimulated hMSCs were applied to SOD1$^{G93A}$ mice by intrathecal injection (1×10$^6$ cells, 1 million cells per injection in 50 µl DMEM/F12) as lumbar puncture at the vertebra L4/5 level and by intramuscular injection (0.5×10$^6$ cells per injection in 50 µl DMEM/F12, two injections per muscle) into hind limb gastrocnemius muscles. Red fluorescent beads were co-injected as an injection marker in the amount of 0.5 µl beads solution/50 µl cell suspension (LifeTechnologies, catalog #F8793, excitation/emission=580/605, 40 nm diameter, 5% solid solution, Azide free). As an immunosuppressant drug, cyclosporine was injected daily at 10 mg/kg body weight by intraperitoneal injection from one day prior to cell injection. The red fluorescent beads were detected near the injection sites (FIGS. 7A, 7C). The injected hMSCs were successfully detected seven days after the injections by immunohistochemistry using anti-human nuclear protein Ku80 antibody (Abcam, Cat #AB80592) and anti-human cytosolic protein STEM121 antibody (Takara Bio, Cat #Y40410) (FIGS. 7B, 7D). Neurofilament staining (Developmental Studies hybridoma bank, 2H3) was used to visualize the spinal cord tissue. DAPI staining was used to visualize nucleus position. These data demonstrate that the hMSCs injected in SOD1$^{G93A}$ mice survived in skeletal muscles and in subarachnoid space around spinal cords for at least seven days.

Figure 8A:
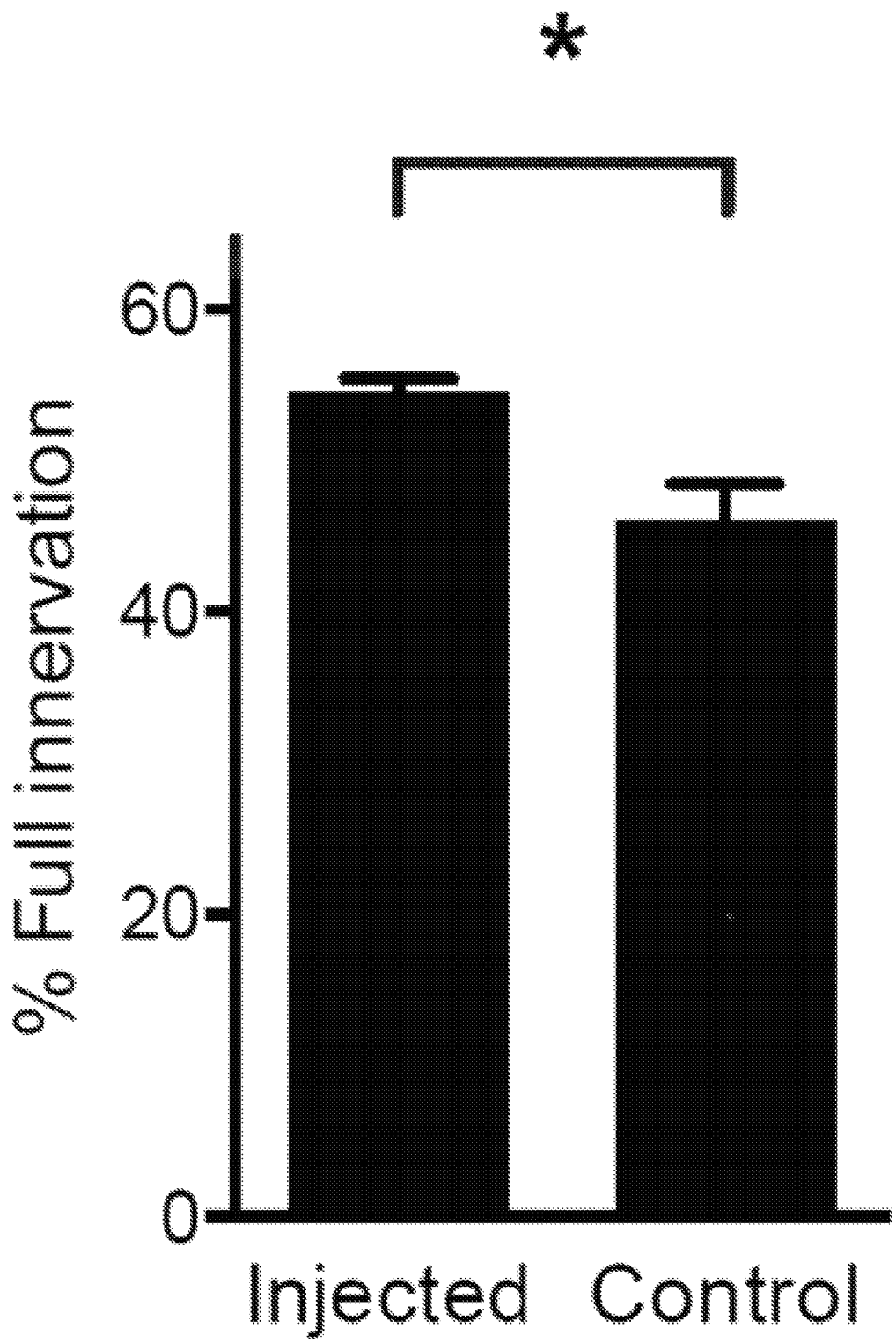
FIGS. 8A, 8B and 8C are graphs depicting the effects of human MSCs on NMJ innervation rate in SOD1$^{G93A}$ mice.
Figure 8B:
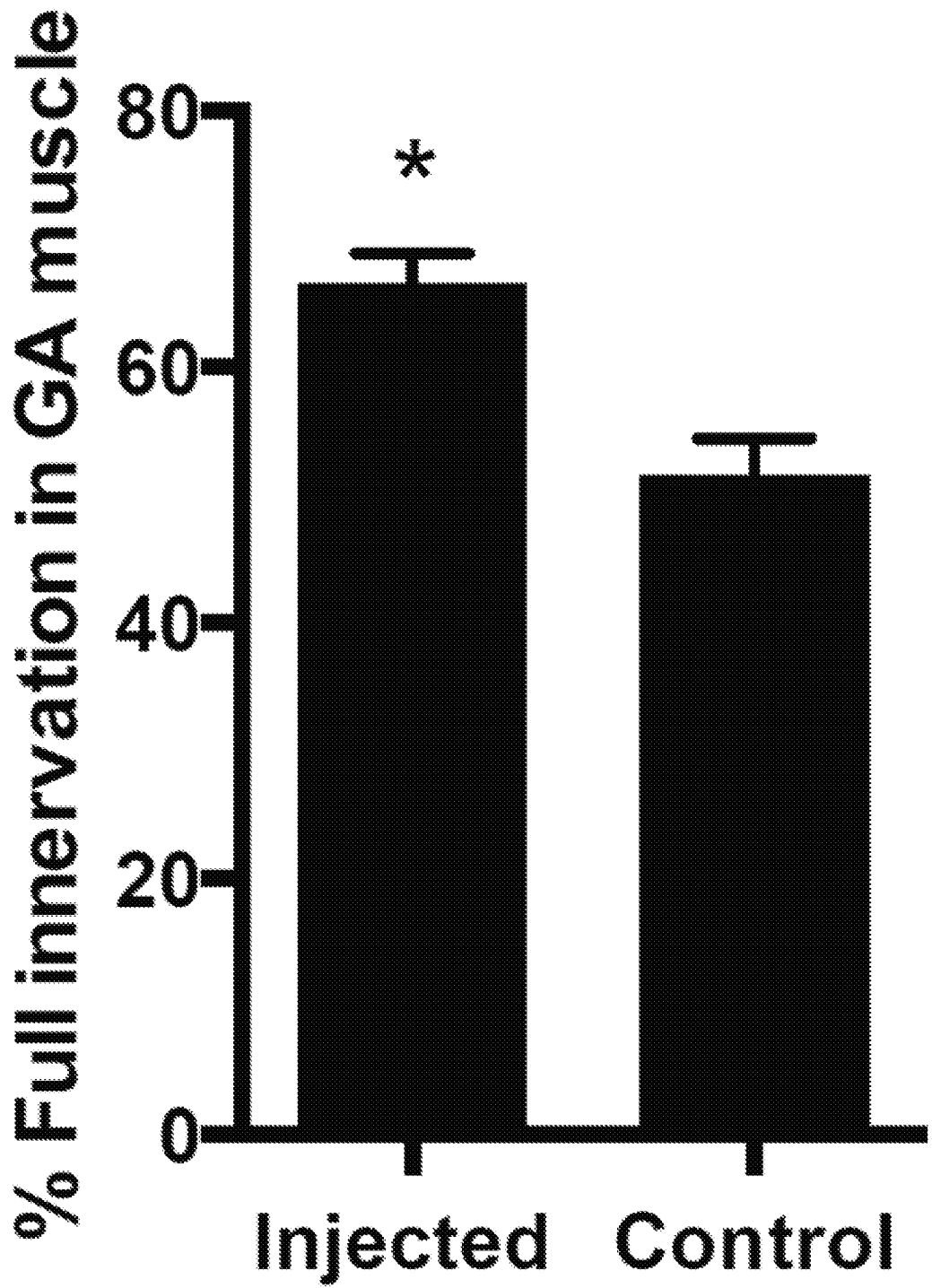

Finally, NMJ innervation rates of gastrocnemius muscles injected with hMSCs were analyzed using an immunohistochemistry based method. Non-injected gastrocnemius muscles of the contralateral hind limb were quantified as controls. NMJ innervation rate was significantly higher in gastrocnemius muscles injected with hMSCs at postnatal day (P) 60 and dissected for innervation analysis at P115 compared to that of contralateral non-injected gastrocnemius muscles (FIG. 8A). A similar difference was observed in gastrocnemius (FIG. 8B) and quadriceps (FIG. 8C) muscles injected with hMSCs at P90 and dissected at P111. These results demonstrated that injected hMSCs ameliorated NMJ denervation in SOD1$^{G93A}$ mice. The results indicate that MSCs ameliorated NMJ denervation by secreting biologically active synapse organizer (laminin β2) and neurotrophic factors (BDNF, GDNF, and VEGF).

The activated hMSCs may be administered to treat a disease for which administration of neurotrophic factors is beneficial in a subject in need thereof. For example, the activated hMSCs may be administered to treat a neurodegenerative disease. The neurodegenerative disease may be a motor neuron disease. Specific examples of motor neuron diseases include primary lateral sclerosis, familial amyotrophic lateral sclerosis, Werdnig-Hoffmann diseases, distal spinal muscular atrophy, familial spinal muscular atrophy, scapular fibular spinal muscular atrophy, juvenile progressive muscular atrophy, infantile progressive muscular atrophy, infant progressive bulbar palsy, diffuse atrophic paralysis, pseudobulbar palsy, amyotrophic lateral sclerosis, bulbar palsy, juvenile unilateral upper-limb muscular atrophy, progressive bulbar palsy, progressive muscular dystrophy, spinal progressive muscular atrophy, traumatic bulbar palsy, spinobulbar muscular atrophy, cervical spondylotic muscular atrophy, and spinal muscular atrophy at all ages. In some embodiments, the activated hMSCs may be administered to treat ALS in a subject. Treatment of ALS may comprise improving one or more symptoms of ALS in the subject. For example, administration of the activated hMSCs may promote growth and/or survival of one or more motor nerve terminals at a neuromuscular junction in the subject. Administration of the activated hMSCs may ameliorate denervation at a neuromuscular junction in the subject.

The activated hMSCs may be administered to the subject by any suitable route. In preferred embodiments, the activated hMSCs are administered parenterally (e.g., intravenous, subcutaneous, intracutaneous, intramuscular, intraarticular, intraarterial, intrasynovial, intrasternal, intrathecal, intralesional, intranasal, or intracranial injection).

Any suitable dosage of the hMSCs may be administered to the subject to achieve the desired result. It will be appreciated that appropriate dosages of the activated hMSCs can vary from patient to patient. Determining the optimal dosage will generally involve the balancing of the level of therapeutic benefit against any risk or deleterious side effects of the treatments. The selected dosage level will depend on a variety of factors including, but not limited to, the route of administration, the time of administration, the duration of the treatment, other drugs, compounds, and/or materials used in combination, and the age, sex, weight, condition, general health, and prior medical history of the patient. In general, a suitable dose of the activated hMSCs is in the range of about $1\times10^4$ cells/injection to about $1\times10^8$ cells/injection. For example, about $1\times10^4$, about $1\times10$, about $1\times10^6$, about $1\times10^7$, or about $1\times10^8$ cells may be administered to the subject in each injection.

The hMSCs may be administered to the subject once a day, or multiple times over the course of the day. For example, hMSCs may be administered to the subject in a single dose once per day. As another example, the hMSCs may be administered to the subject twice per day, three times per day, four times per day, or five times per day. The hMSCs may be administered to the subject for any suitable duration of time necessary to achieve the desired result. The total duration of treatment and the frequency of administration will depend on the survival of the injected cells and the lifespan of the patient. For example, the hMSCs may be administered to the subject for at least 1 day, at least 2 days, at least 3 days, at least 4 days, at least 5 days, at least 6 days, at least 1 week, at least 2 weeks, at least 3 weeks, at least 1 month, at least 2 months, at least 3 months, or at least 6 months. In some embodiments, the hMSCs may be administered to the subject intermittently for the duration of the patient's life span. For example, the hMSCs may be administered to the subject once every week, once every two weeks, once every month, once every two months, once every three months, once every four months, once every five months, or once every six months for the duration of the patient's life span.

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting the scope of the disclosure. The disclosures of all journal references, U.S. patents, and publications referred to herein are hereby incorporated by reference in their entireties. The present disclosure has multiple aspects, illustrated by the following non-limiting examples.

4. Examples

Example 1: IGF-1 Stimulated Production of Laminin β2 Protein and Ameliorated NMJ Denervation Rate of SOD1$^{G93A}$ Mice Human MSCs were cultured for 72 hrs in normal culture medium (control), or in stimulation medium (without IGF) or in stimulation medium with 20 ng/mL IGF-1 (with IGF). The stimulation media consisted of serum-free DMEM/F12 media supplemented with 20 ng/mL human bFGF 146aa, 20 ng/mL human EGF, and 10 uL/mL N2 supplement. For an additional 72 hrs, the MSCs were treated with the following serum-free media with or without 20 ng/mL IGF-1: 0.5 mM IBMX, 1 mM dibutryl cAMP, 20 ng/mL human bFGF-146aa, 50 ng/mL human Heregulin β1, 5 ng/mL human PDGF-AA.

Laminin β2 protein expression level was determined by western blot detection and densitometry analysis. The data were normalized to the laminin β2 protein expression level of the control group. MSCs treated with stimulation media with IGF-1 exhibited significantly higher level of laminin β2 compared to the control group or the stimulation media without IGF-1 group (FIG. 1A). Graph shows mean±SEM from n=3 independent experiments. Asterisks indicate significant differences by one-way ANOVA and Tukey's multiple comparisons test, P<0.05.

Figure 1B:
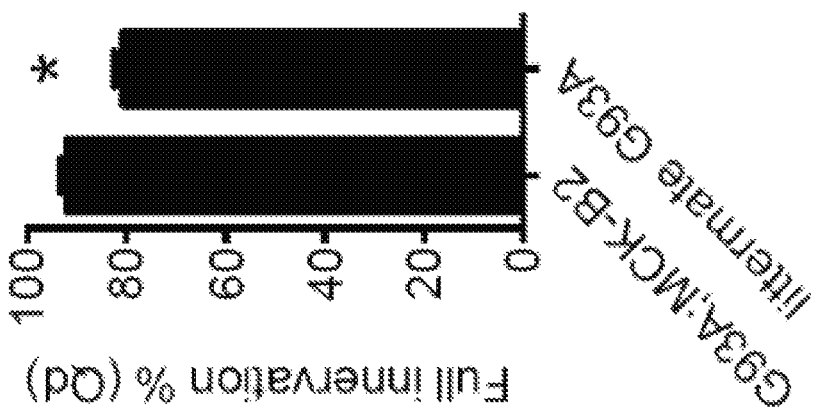
Figure 1B:
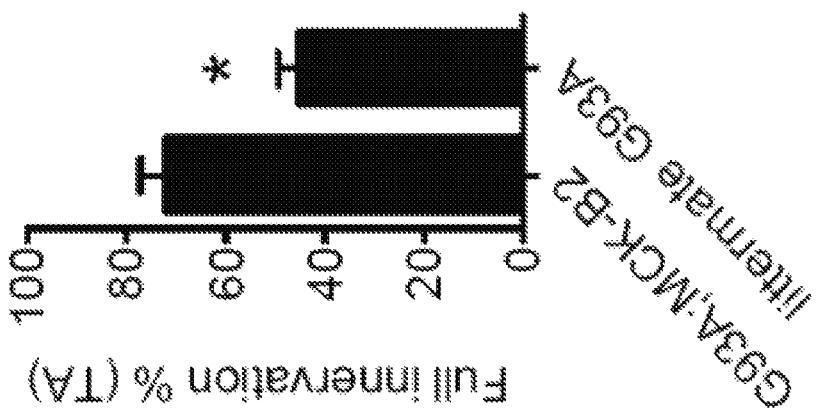
Figure 1B:
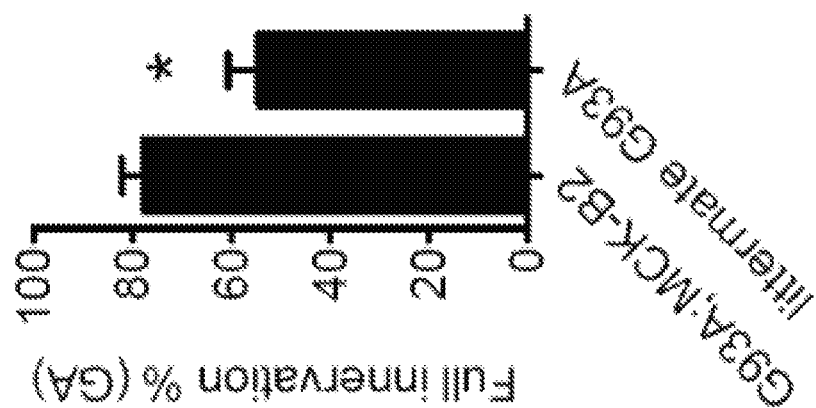

SOD1$^{G93A}$ mice were mated with transgenic mice expressing rat laminin β2 gene in skeletal muscles (MCK-B2). Rates of fully innervated NMJs were compared at postnatal day 57 between SOD1$^{G93A}$; MCK-B2 and littermate SOD1$^{G93A}$ mice to consider the mixed genetic background caused by mating with the transgenic mice (FIG. 1B). SOD1$^{G93A}$; MCK-B2 mice showed higher innervation rate than littermate SOD1$^{G93A}$ mice in gastrocnemius (left), tibialis anterior (center), and quadriceps femoris (right) muscles. Graphs show mean±SEM, 89-219 NMJs from n=6 for SOD1$^{G93A}$; MCK-B2 mice and n=4 for SOD1$^{G93A}$ mice. Asterisks indicate significant differences by un-paired t-test, P<0.01.

In accordance with the embodiments of the present disclosure, materials and methods for IGF-1 stimulated production of synaptic organizing agents such as laminin β2, as well as various neurotrophic factors, can include seeding MSCs at 12,000 cells/cm$^2$ in DMEM/F12+10% FBS; treating the cells with the following serum-free media for 72 hrs: DMEM/F12 (contains 2.5 mM L-glutamine), 1 mM dibutryl cAMP, 20 ng/mL human bFGF-146aa, 50 ng/mL human Heregulin § 1, 5 ng/mL human PDGF-AA, and 20 ng/mL human IGF-1.

In accordance with the embodiments of the present disclosure, materials and methods for IGF-1 stimulated production of synaptic organizing agents such as laminin β2, as well as various neurotrophic factors, can also include seeding MSCs at 12,000 cells/cm$^2$ in DMEM/F12+10% FBS and allowing growth for 2 days ~70% confluent. A first phase of the protocol (Phase 1) can include treating the cells with the following serum-free media for 72 hrs: DMEM/F12 (contains 2.5 mM L-glutamine), 20 ng/mL human bFGF 146aa, 20 ng/mL human EGF, and 10 uL/mL N2 supplement. A second phase of the protocol (Phase 2) can include treating cells with the following serum-free media for an additional 72 hrs: DMEM/F12 (contains 2.5 mM L-glutamine), 0.5 mM IBMX, 1 mM dibutryl cAMP, 20 ng/mL human bFGF-146aa, 50 ng/mL human Heregulin β1, 5 ng/mL human PDGF-AA, and 20 ng/mL human IGF-1.

In accordance with the embodiments of the present disclosure, materials and methods for IGF-1 stimulated production of synaptic organizing agents such as laminin β2, as well as various neurotrophic factors, can also include growing human MSCs in Dulbecco's Modified Eagle Medium/Nutrient Mixture F-12 (DMEM/F12) containing 10% FBS to 70% confluency in 10 cm dish. Next, hMSCs can be stimulated for 72 hours in DMEM/F12 media (2.5 mM L-glutamine) supplemented with human bFGF (20 ng/ml), human EGF (20 ng/ml), and N2 supplement (10 μl/ml). Next, hMSCs can be stimulated additionally for 72 hours in DMEM/F12 media (2.5 mM L-glutamine) supplemented with 0.5 mM IBMX, 1 mM dibutyryl cAMP, human bFGF (20 ng/ml), human heregulin 1 (50 ng/ml), human PDGF (5 ng/ml), and human IGF-1 (20 ng/ml).

The non-differentiated state of the stimulated MSCs can be confirmed by the detection of MSC cell surface markers. For example, the non-differentiate state of the stimulated MSCs can be confirmed by the detection of one or more of CD73, CD90, and CD105. Alternatively or in combination, the non-differentiated state of the stimulated hMSCs can be confirmed by the absence of negative cell surface markers. For example, the non-differentiated state of the stimulated hMSCs can be confirmed by the absence of one or more of CD11b, CD19, CD34, CD45, and HLA-DR.

Figure 2A:
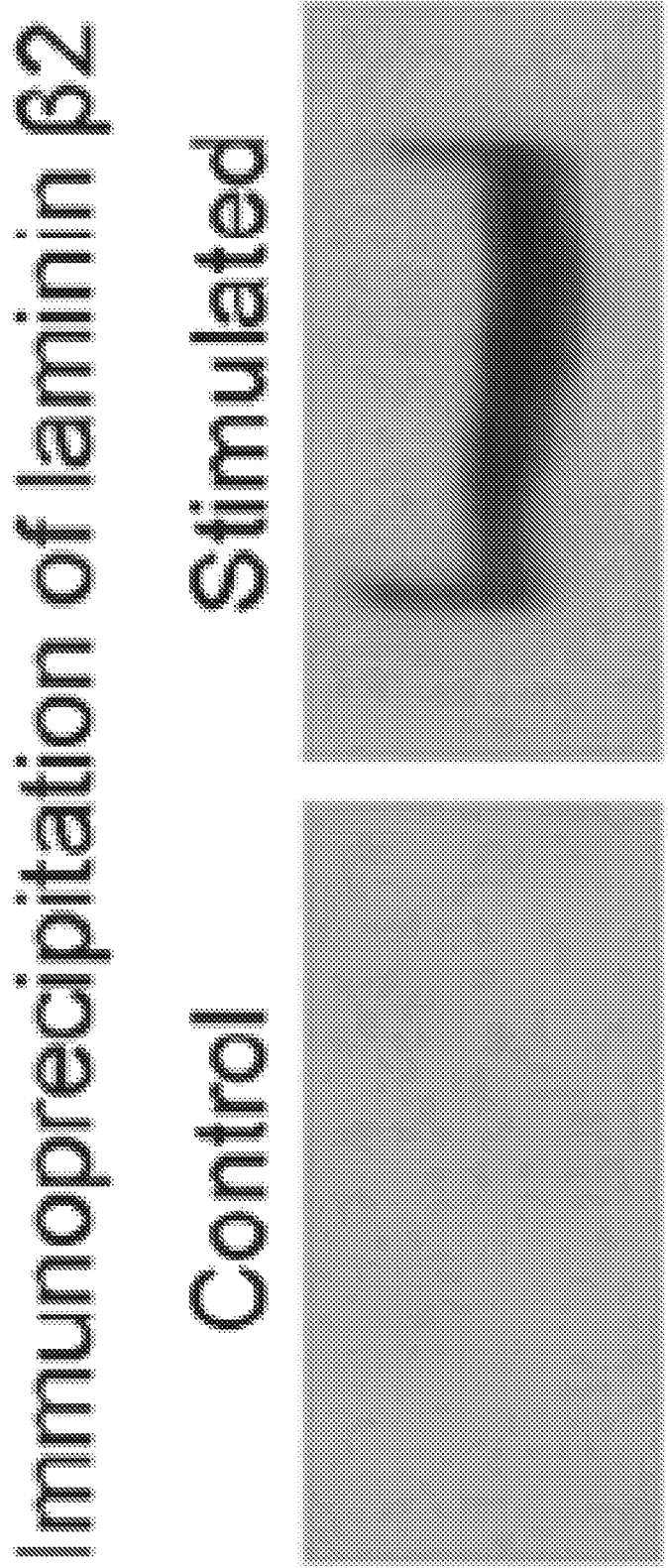
FIGS. 2A, 2B, 2C, 2D, 2E, 2F, and 2G are graphs and images depicting the effects of cell culture medium based stimulation on secretion of a synapse organizer laminin β2 (2A, 2B, 2G) and neurotrophic factors (2C, 2D, 2E, 2F) in human MSCs.
Figure 2B:
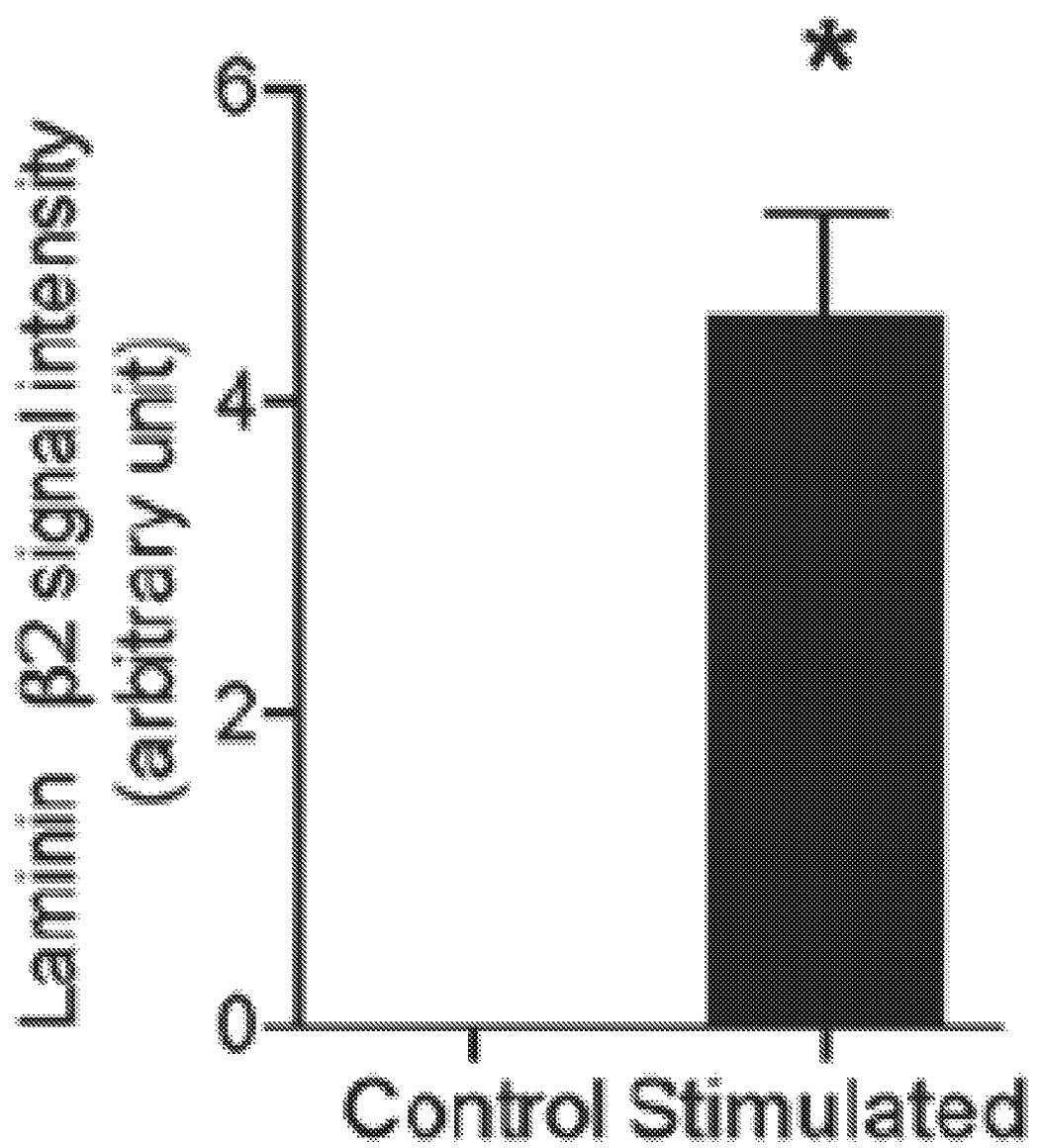
Figure 2C:
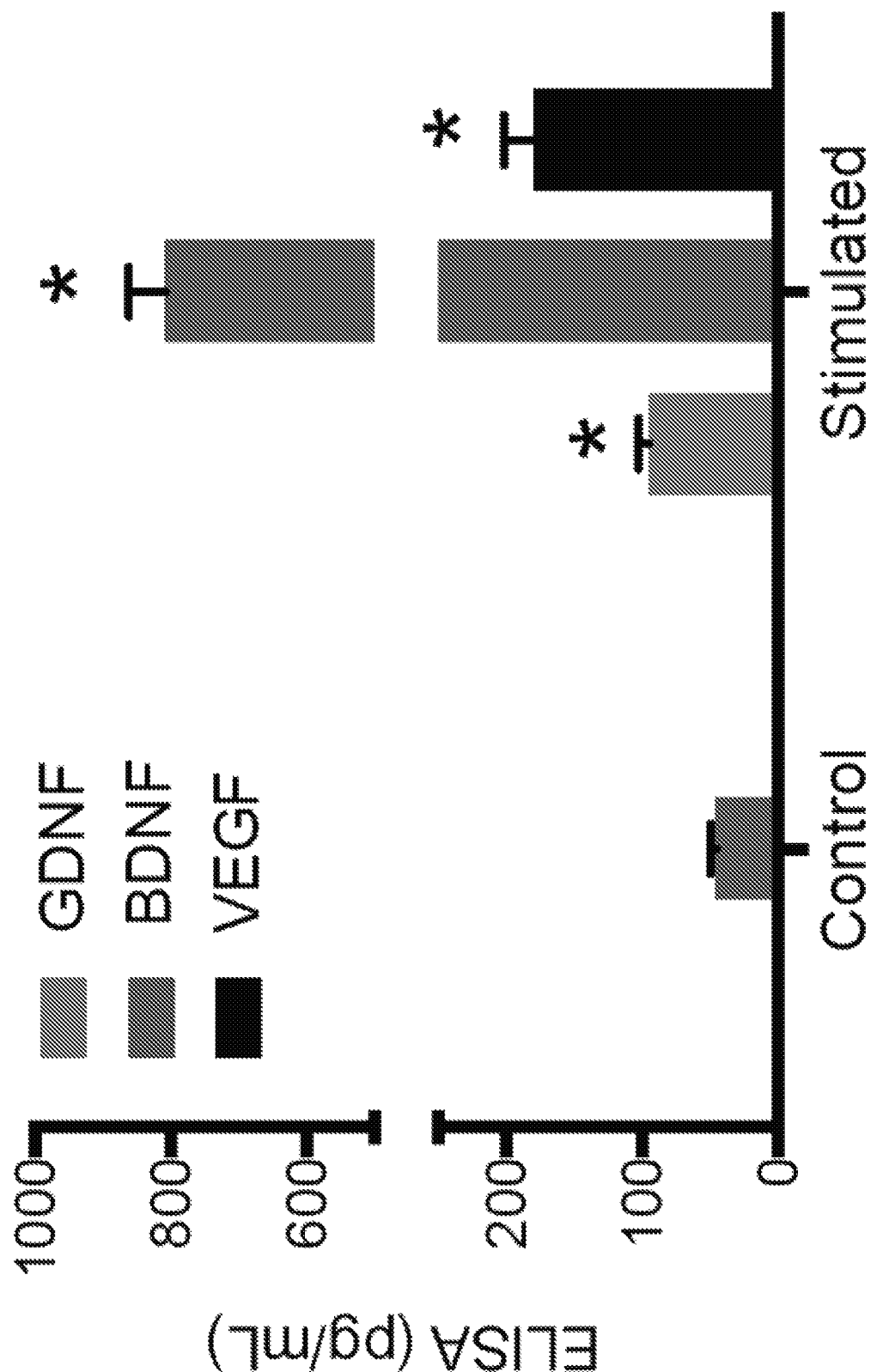
Figure 2D:
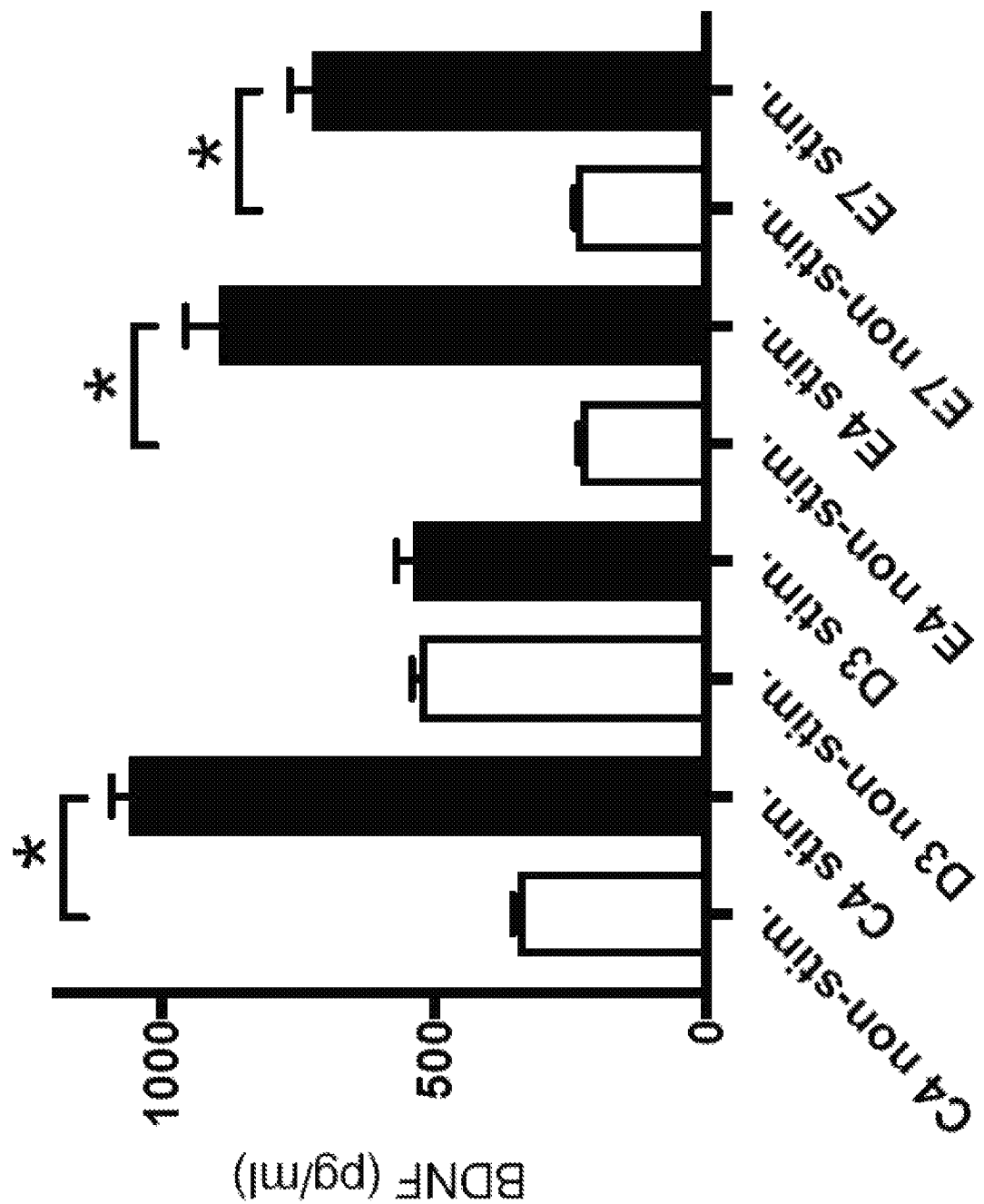
Figure 2E:
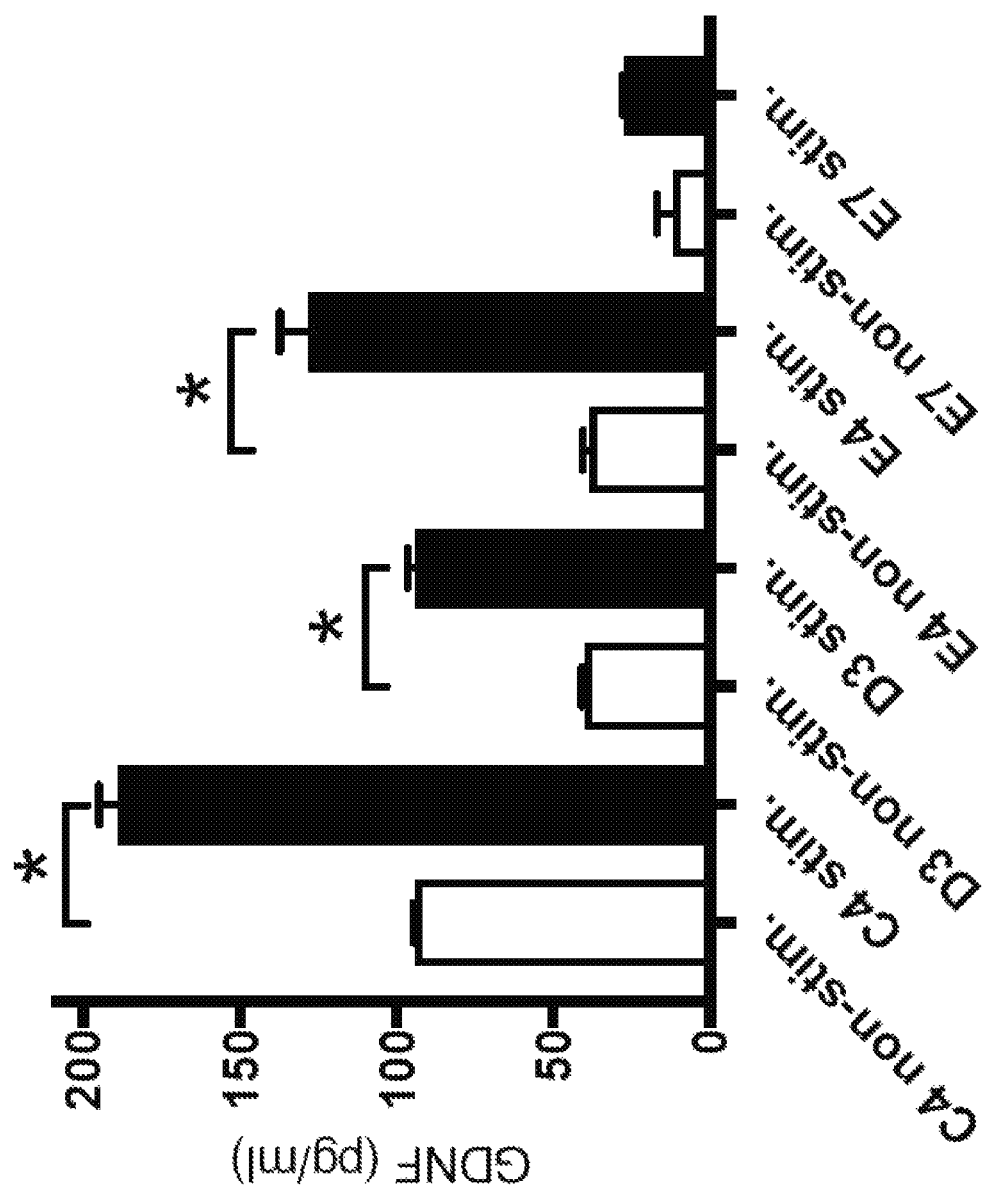
Figure 2F:
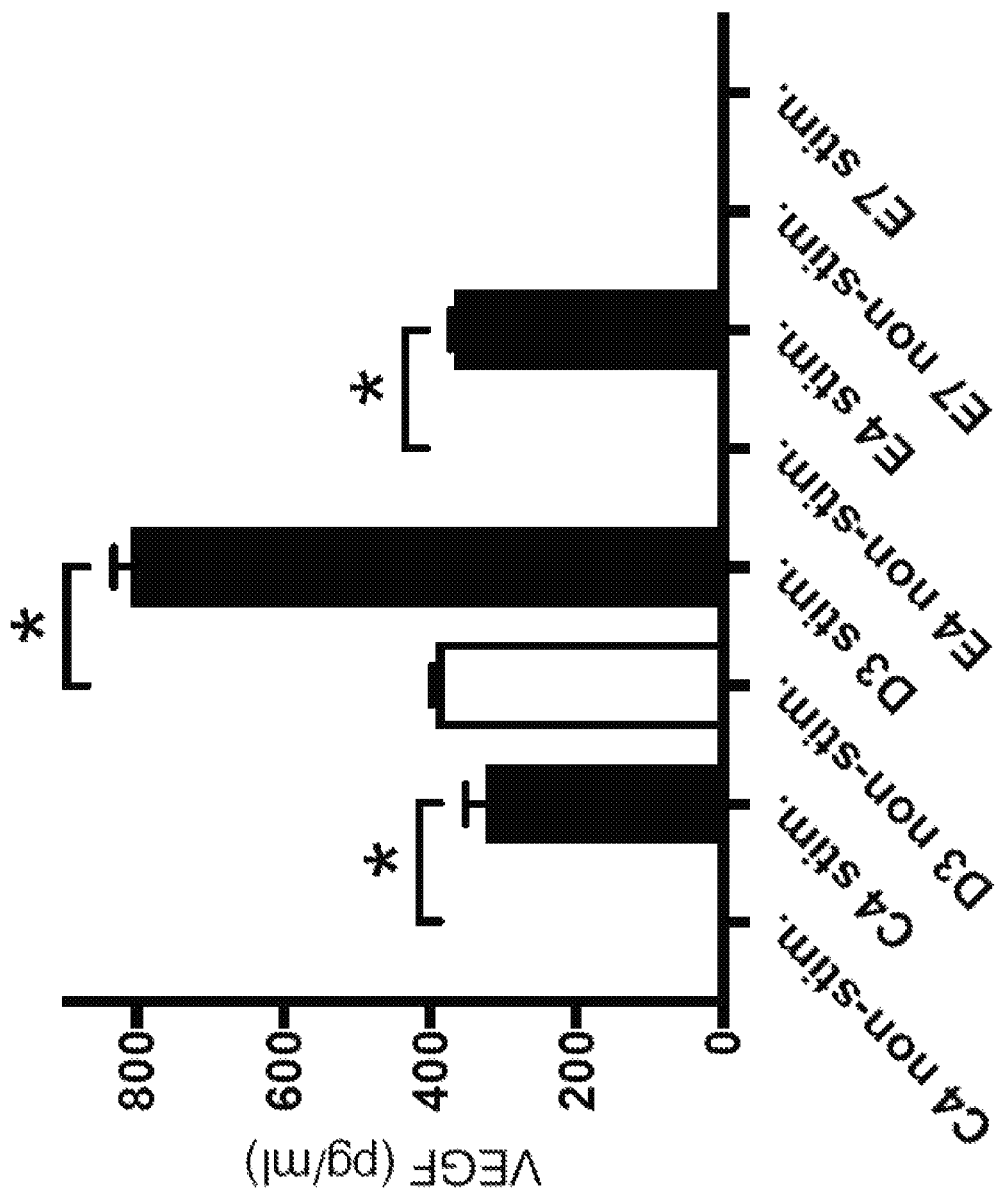
Figure 2G:
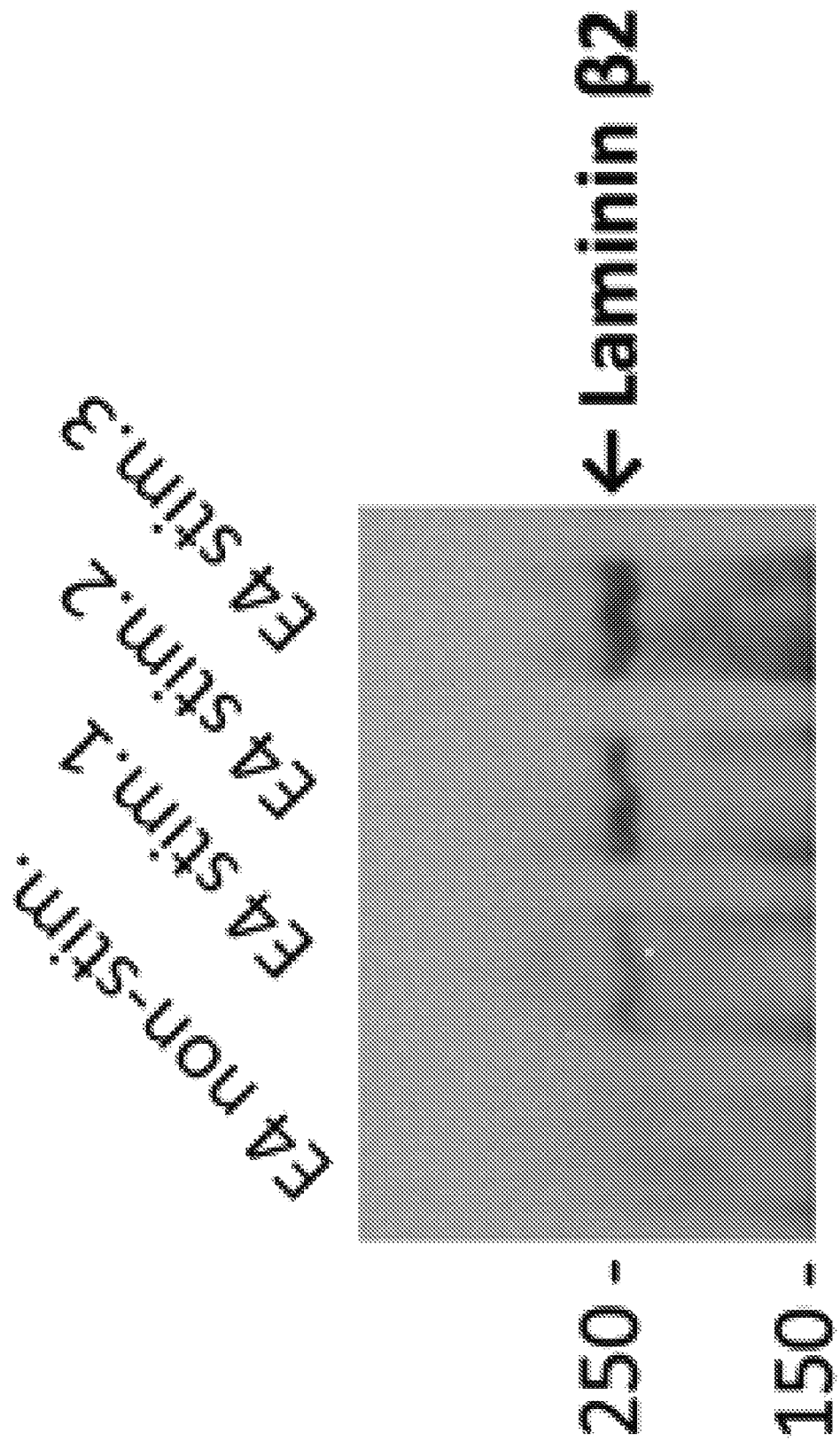

Example 2: Human MSCs Increase Secretion of a Synapse Organizer and Neurotrophic Factors after Culture Medium Based Stimulation FIGS. 2A-2C show the effects of cell culture medium based stimulation in human MSCs derived from Donor 1 (Cord #4). After six days in stimulation medium, hMSCs increased secretion of synapse organizer (laminin β2) and neurotrophic factors (BDNF, GDNF, and VEGF), which were confirmed using immunoprecipitation/Western blotting (FIGS. 2A-2B, FIG. 2G) and ELISA (FIG. 2C, FIG. 2D, FIG. 2E, FIG. 2F), respectively. Asterisks show significant difference by (B) t-test and (C) two-way ANOVA. FIGS. 2D-2E show the effects of cell culture medium based stimulation in human MSCs derived from donor 1 and three other donors, D00003, E00004, and E00007. As shown in FIG. 2D, hMSCs from donor 1 (Cord #4, C4), donor 4 (E0004, E4), and donor 7 (E0007, E7) increased secretion of BDNF in response to stimulation, but hMSCs from donor 3 (D0003, D3) did not respond to stimulation in this experiment. As shown in FIG. 2E hMSCs from donor 1 (Cord #4, C4), donor 3 (D0003, D3), and donor 4 (E0004, E4) increased secretion of GDNF in response to stimulation, but hMSCs from donor 7 (E0007, E7) did not respond to stimulation in this experiment. As shown in FIG. 2F, hMSCs from donor 1 (Cord #4, C4), donor 3 (D0003, D3), and donor 4 (E0004, E4) increased secretion of VEGF in response to stimulation, but hMSCs from donor 7 (E0007, E7) did not respond to stimulation in this experiment. As shown in FIG. 2G, hMSCs from donor 4 (E0004, E4) increased secretion of the synapse organizer (laminin β2) after culture medium based stimulation in three independent trials (E4 stim. 1, E4 stim. 2, and E4 stim. 3) compared to hMSCs without stimulation (E4 non-stim.). Secretion of synapse organizer (laminin β2) was confirmed using immunoprecipitation and western blot detection.

Example 3: Secreted Proteins from Human MSCs Enhanced the Survival of Spinal Cord Motor Neurons Motor neurons were purified from mouse spinal cords and cultured as dissociated cells in medium containing 25% of hMSC conditioned medium. These motor neurons survived at significantly higher rate than motor neurons in medium containing 25% new culture medium that has not been conditioned with hMSC (FIG. 3A). Motor neurons cultured with 0.1 ng/ml human GDNF served as a positive control. Representative images of cultured motor neurons in phase contrast (left) and color traced to indicate their axons (right; FIG. 3B). Asterisk indicates significant difference by one-way ANOVA and Tukey's multiple comparisons test, $P<0.05$.

Figure 6A:
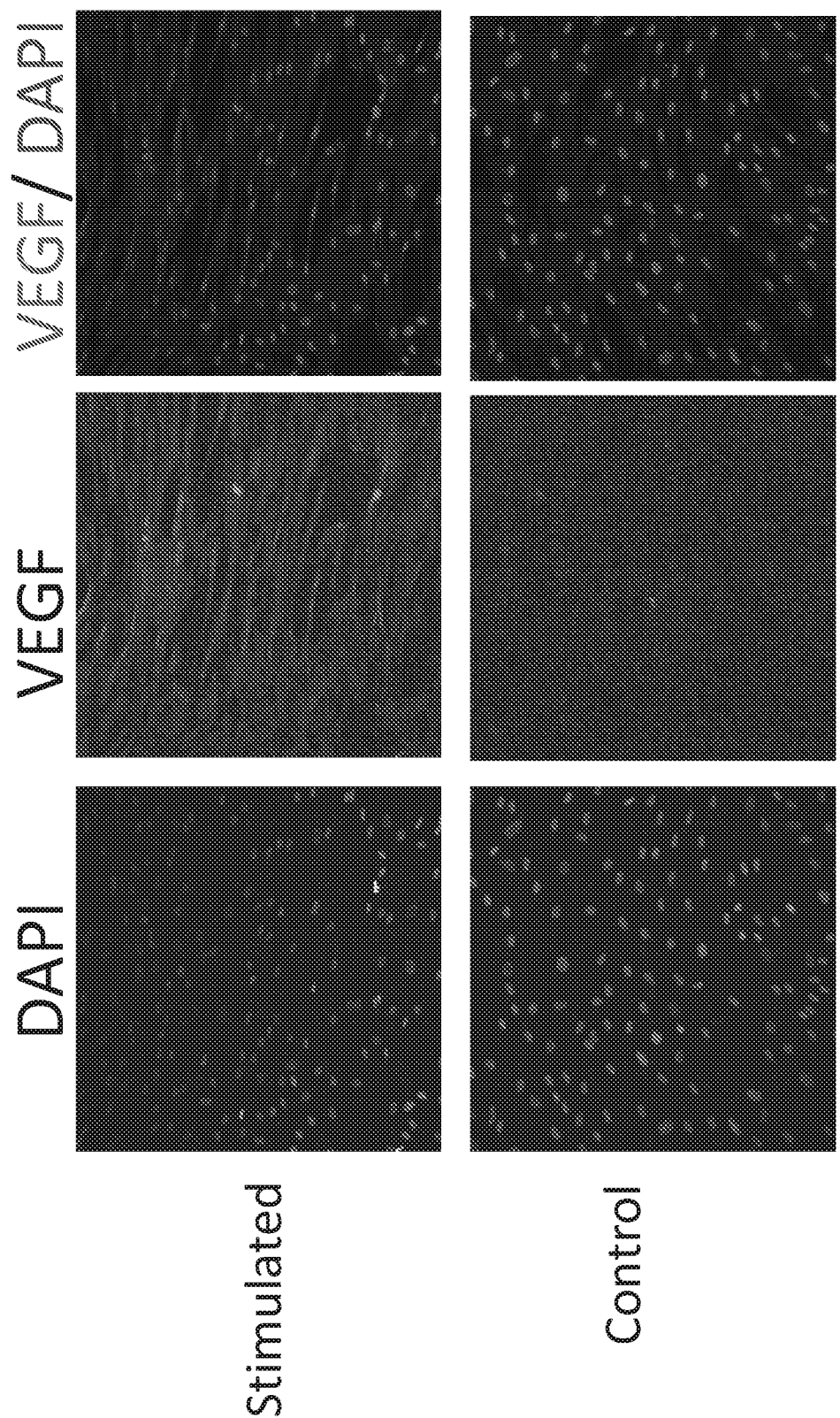
FIGS. 6A, 6B and 6C are graphs and images depicting the effect of the culture medium based stimulation on VEGF protein expression in human MSCs.
Figure 6B:
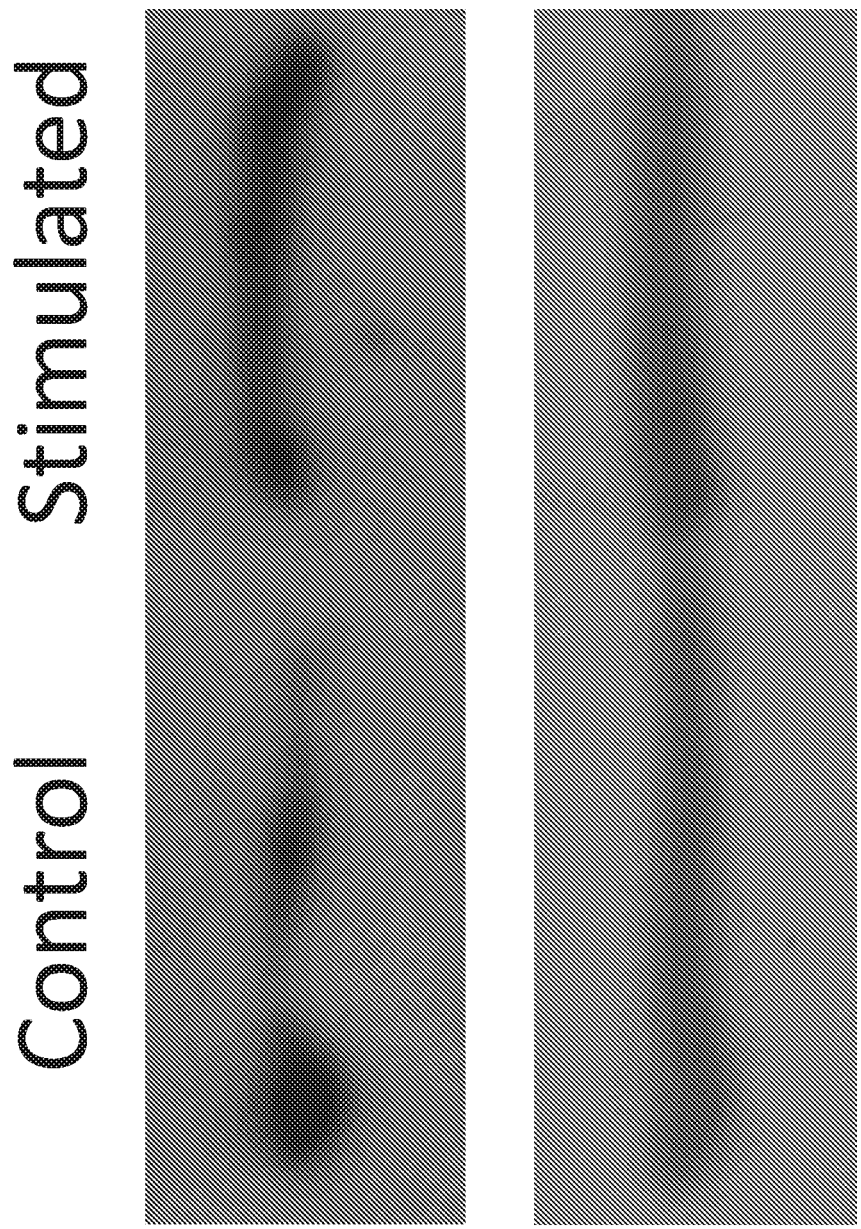
Figure 6C:
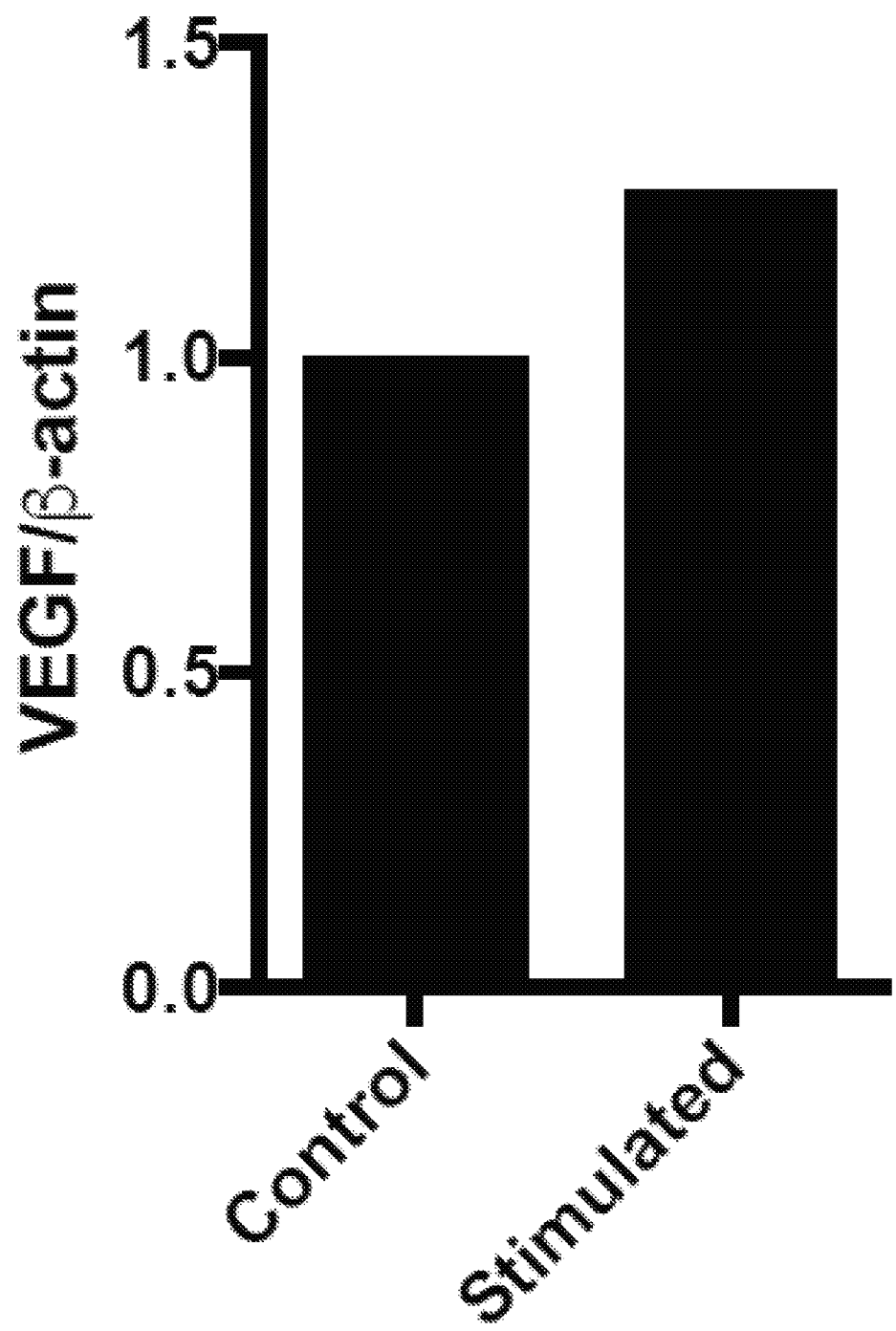

Example 4: Human MSCs Increase Expression of Vascular Endothelial Growth Factor (VEGF) after Culture Medium Based Stimulation MSCs were stimulated with IGF in vitro and VEGF protein expression levels were compared using immunocytochemistry and western blot analysis (FIG. 6). (A) Representative immunofluorescent images demonstrating an increase in VEGF expression level (middle panel and red in the right panel) in stimulated MSCs compared to control, untreated MSCs. (B) VEGF protein expression level determined by western blot analysis and (C) quantification of western blot signal intensity. Sample loading variation was normalized using D-actin detection level (n=1).

Figure 4A:
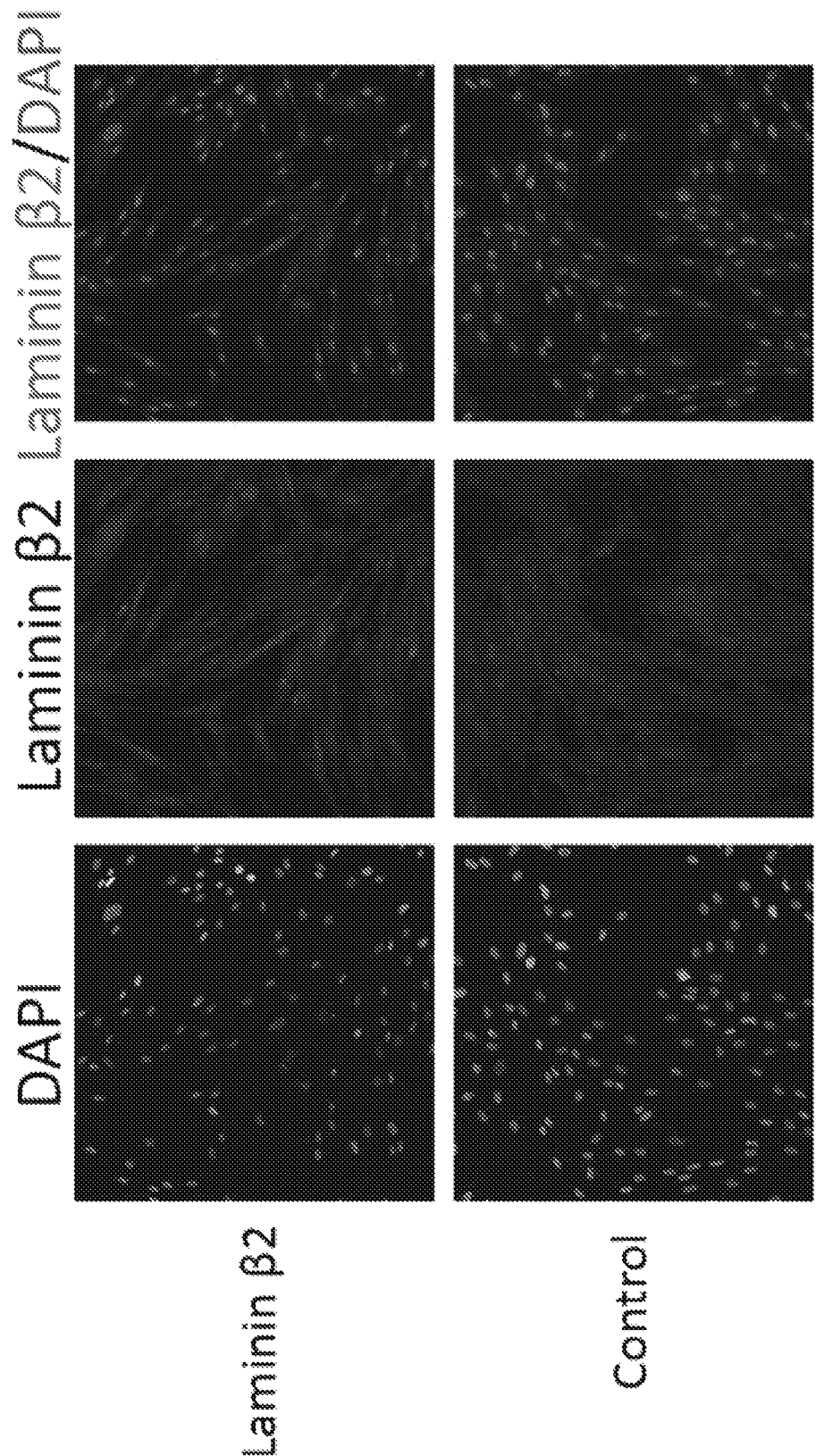
FIGS. 4A, 4B and 4C are graphs and images depicting the effect of the culture medium based stimulation on laminin β2 protein expression in human MSCs.
Figure 4B:
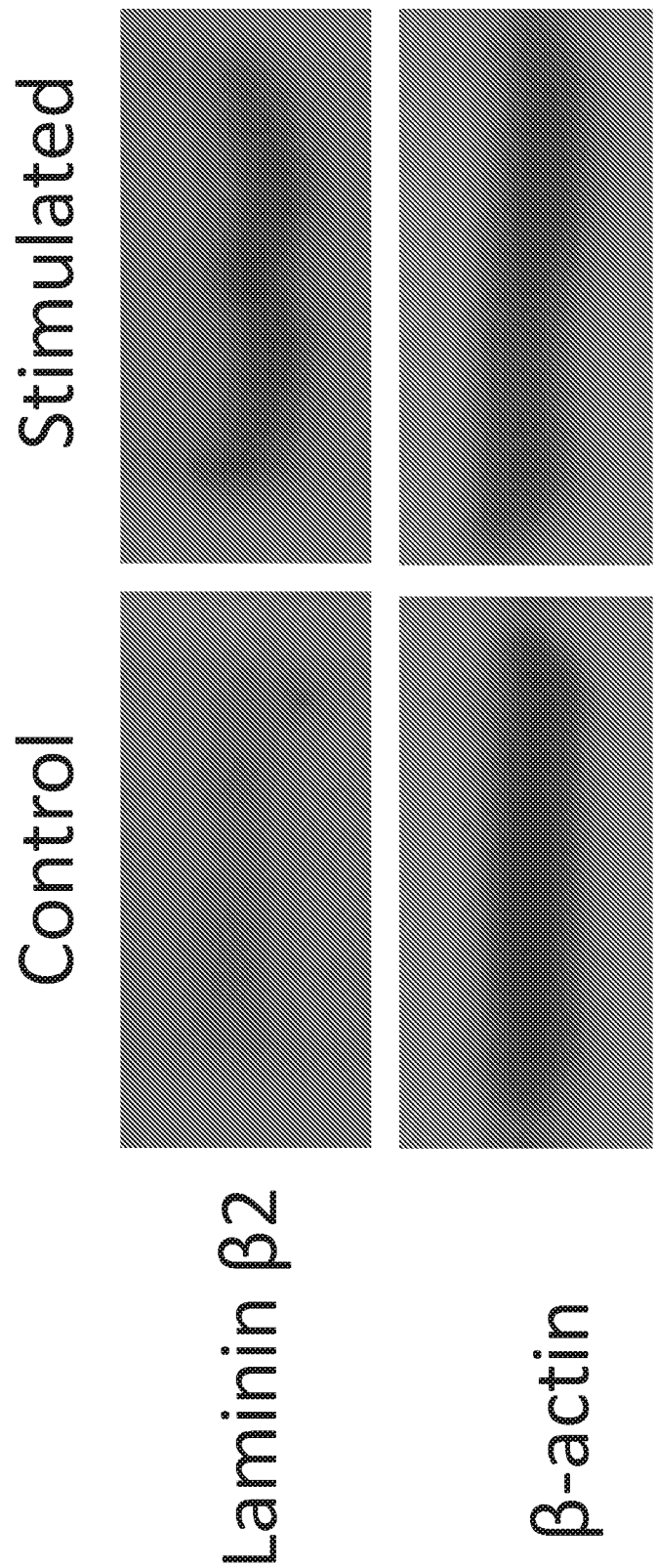
Figure 4C:
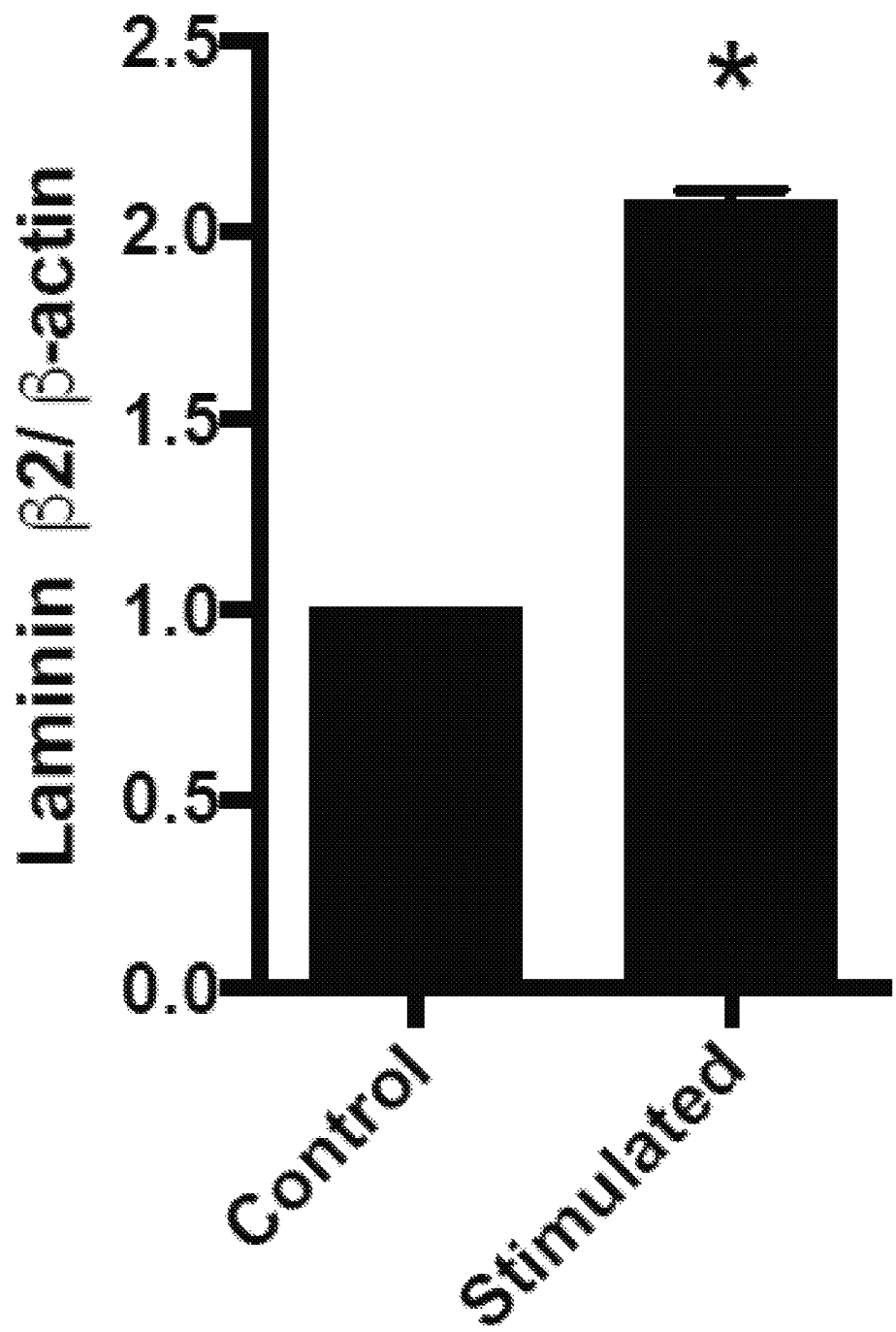

Example 5: Human MSCs Increase Expression of a Synapse Organizer (Laminin β2) after Culture Medium Based Stimulation MSCs were stimulated with IGF in vitro and laminin β2 protein expression levels were compared using immunocytochemistry and western blot analysis (FIG. 4). (A) Representative immunofluorescent images demonstrating an increase in laminin β2 expression level (middle panel and red in the right panel) in stimulated MSCs compared to control, untreated MSCs. (B) Laminin β2 protein expression level determined by western blot analysis and (C) quantification of western blot signal intensity. Sample loading variation was normalized using β-actin detection level (n=1).

Figure 5A:
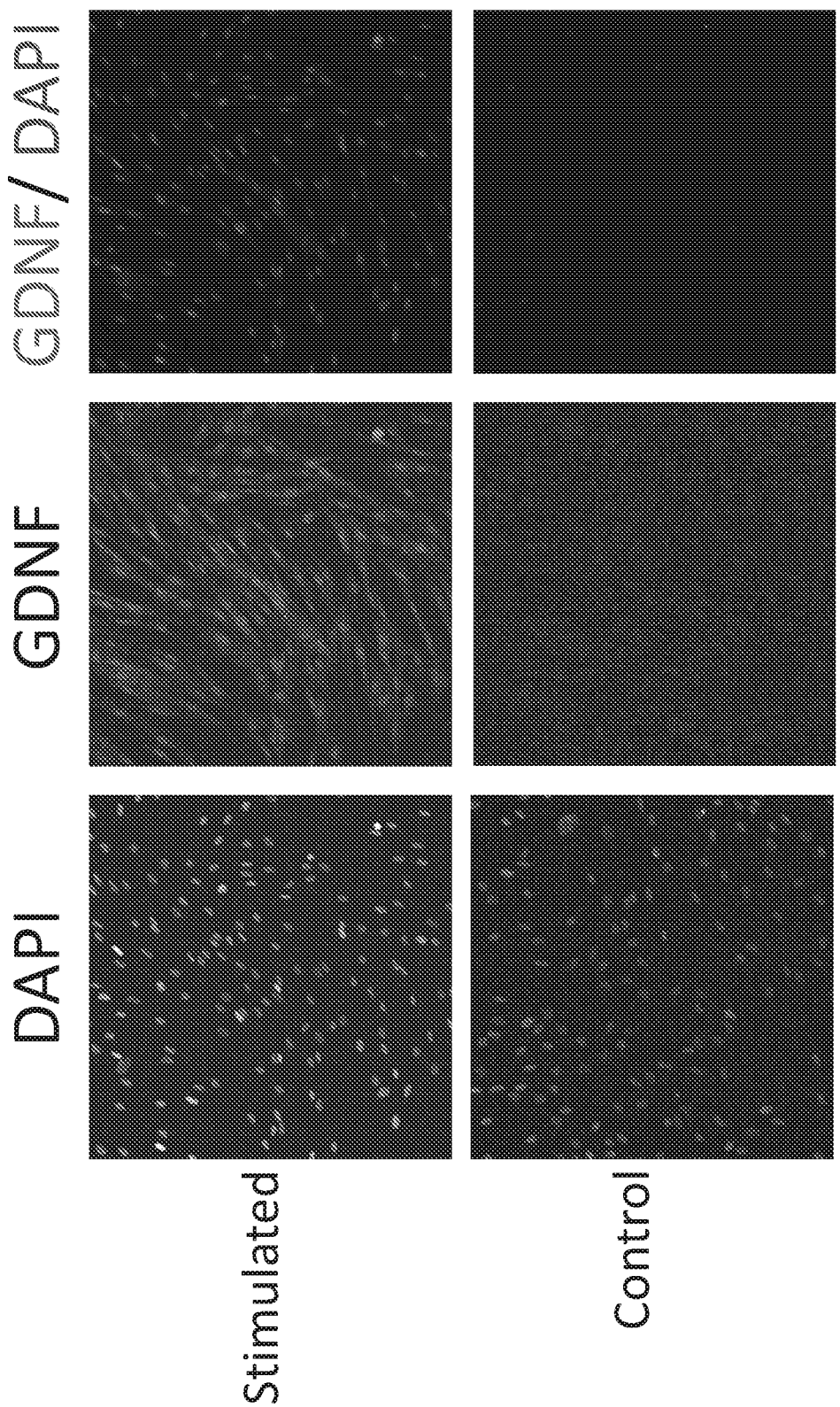
FIGS. 5A, 5B and 5C are graphs and images depicting the effect of the culture medium based stimulation on GDNF protein expression in human MSCs.
Figure 5B:
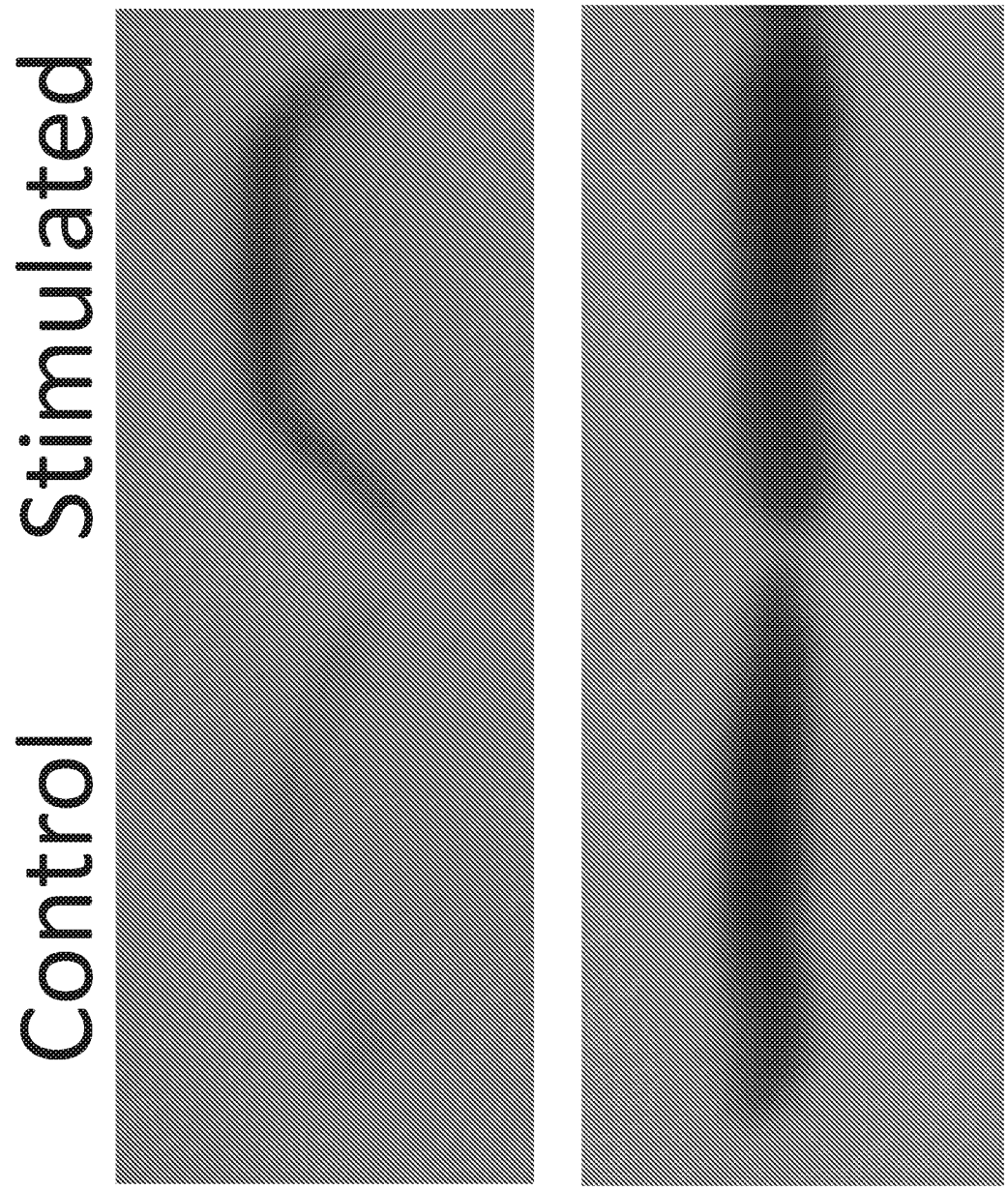
Figure 5C:
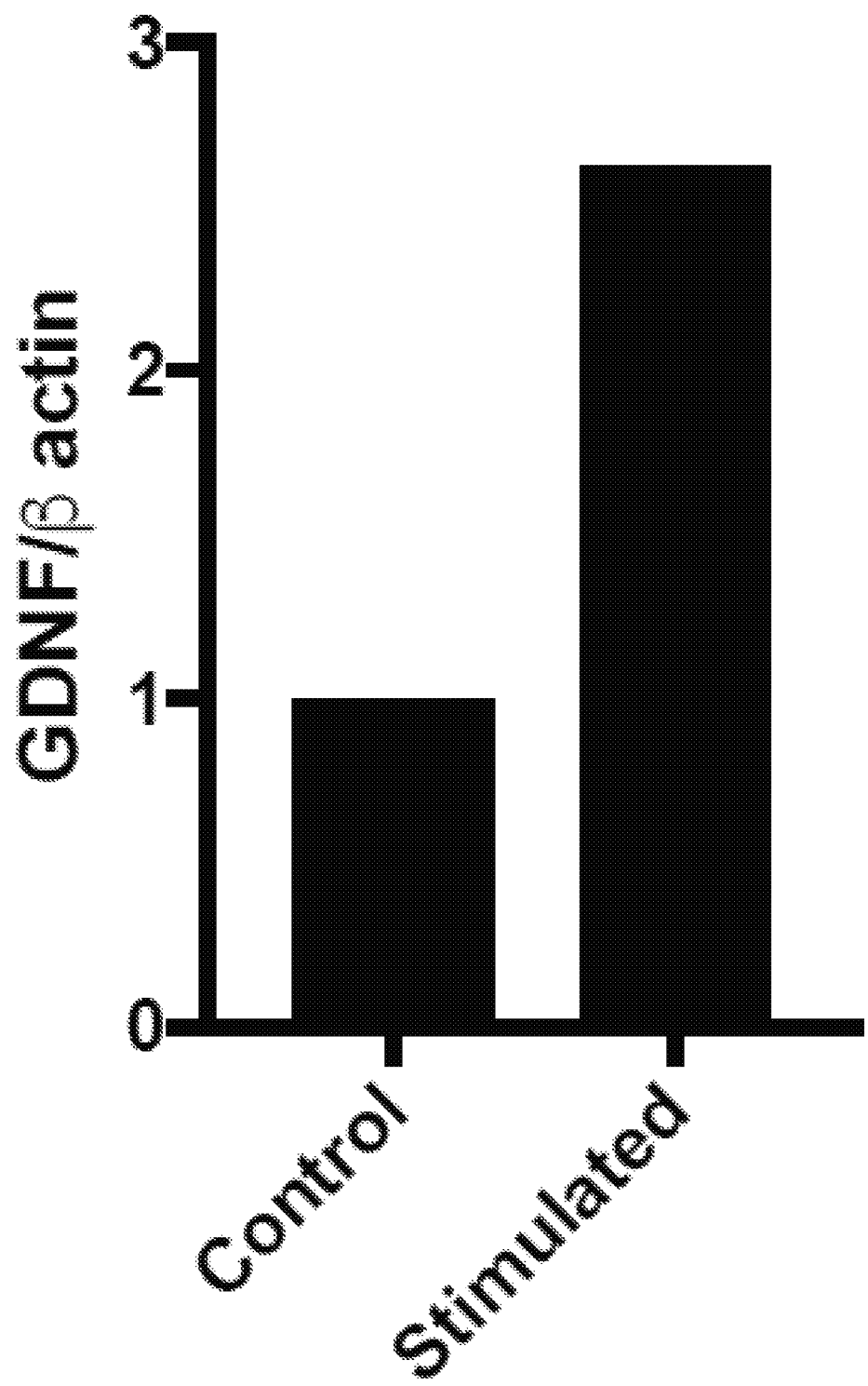

Example 6: Human MSCs Increase Expression of Glial Cell-Derived Growth Factor (GDNF) after Culture Medium Based Stimulation MSCs were stimulated with IGF in vitro and GDNF protein expression levels were compared using immunocytochemistry and western blot analysis (FIG. 5). (A) Representative immunofluorescent images demonstrating an increase in GDNF expression level (middle panel and red in the right panel) in stimulated MSCs compared to control, untreated MSCs. (B) GDNF protein expression level determined by western blot analysis and (C) quantification of western blot signal intensity. Sample loading variation was normalized using β-actin detection level (n=1).

Example 7: In Vivo Injection of hMSCs into ALS Model Mice $SOD1^{G93A}$ mice were dissected seven days after (FIGS. 7A-7B) intramuscular and (FIGS. 7C-7D) intrathecal injection of hMSCs. The injected gastrocnemius muscle is shown with the injection marker red fluorescent beads (FIG. 7A). Intramuscular injected hMSCs were detected in gastrocnemius muscle sections by immunohistochemistry using antibodies against human protein Ku80 (DNA helicase), human protein STEM121 (cytosolic protein), and DAPI (nuclear stain) (FIG. 7B). Representative images show accumulations of injected hMSC inside the muscle. Intrathecal injected spinal cord is shown with the injection marker red fluorescent beads (FIG. 7C). Injected hMSCs were detected in spinal cord sections by immunohistochemistry using antibody that specifically detects human Ku80, mouse neurofilament, and DAPI (FIG. 7D). Representative images show few injected hMSCs on the surface of the spinal cord. Scale Bar: (FIGS. 7A, 7C) 1 mm; (FIGS. 7B, 7D) 20 µm.

Example 8: Human MSCs Ameliorate NMJ Innervation Rate in SOD1$^{G93A}$ Mice

Figure 8C:
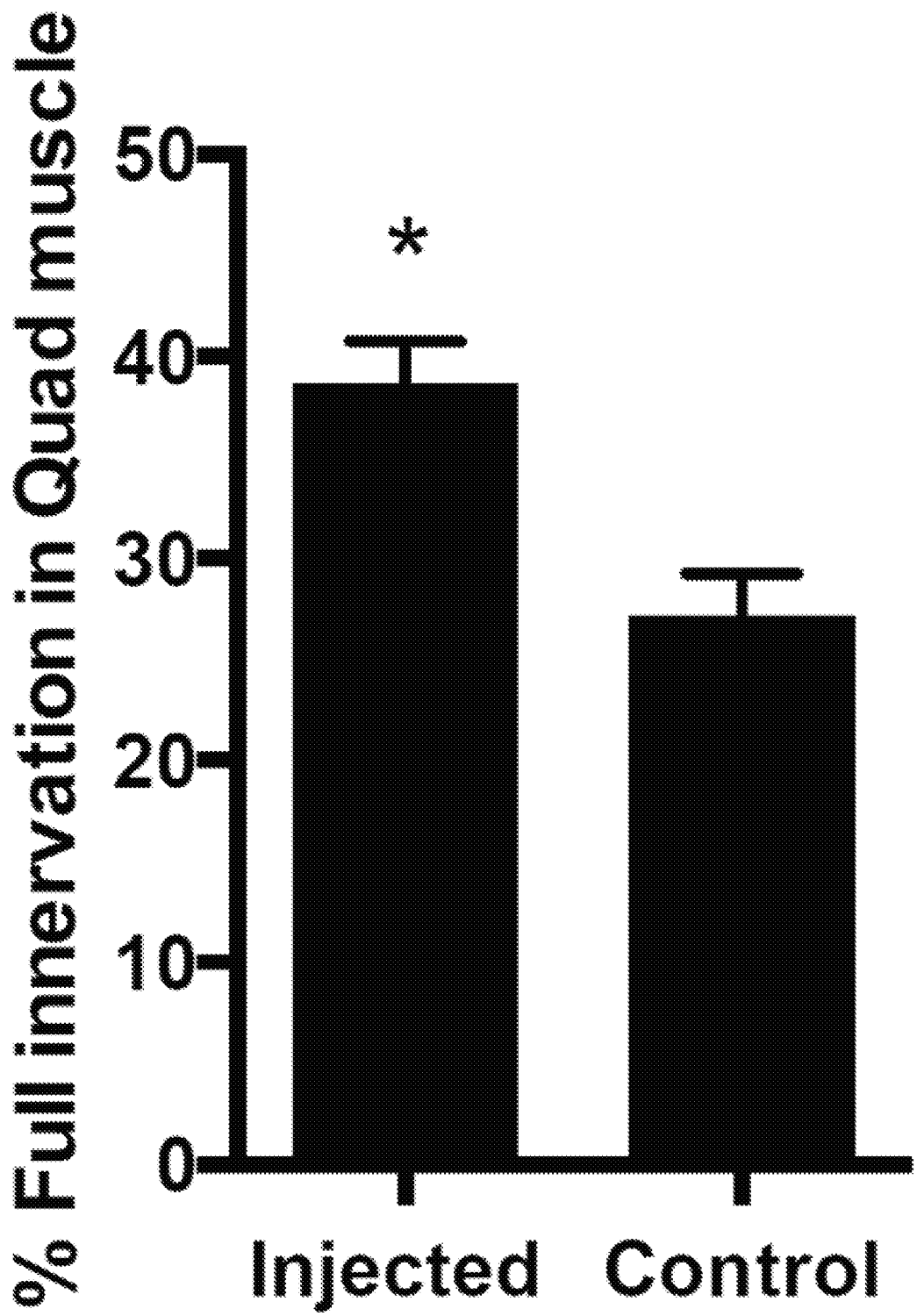

NMJ innervation rate was higher in gastrocnemius muscle that received intramuscular injection of hMSCs at P60 and dissected at P115 compared to that of contralateral non-injected muscle (FIG. 8A). Asterisk indicates significant difference p=0.0188 by unpaired t-test, and n=4 animals. A similar difference was observed in gastrocnemius (FIG. 8B) and quadriceps (FIG. 8C) muscles injected with hMSCs at P90 and dissected at P111. Graph shows mean±SEM from n=6 (FIG. 8B) and n=4 animals (FIG. 8C). Asterisks indicate significant differences by un-paired t-test, P<0.05.

Example 9: Materials and Methods

The manufacturing process for MSCTC-0010, Suspension for Infusion, begins with donated human umbilical cord tissue following child birth at the University of Kansas Hospital Labor and Delivery unit. The umbilical cord pieces (typically 15 to 20 cm long) are accepted if the mother has agreed to the donation and has reviewed and signed an institutional review board-approved informed consent document. The mother must be tested and shown to be free of Human Immunodeficiency Virus (HIV) Types 1 & 2, Hepatitis A, B, and C, *Treponema pallidum, Chlamydia trachomatis, Neisseria* gonorrhea, and HTLV 1 and 2. Umbilical cord pieces were obtained from 4 donors. The cord name, gender of the fetus, gestational age, and age of the mother are shown in Table 1 below.

TABLE 1

| Cord name (by MSC center) | Gender of fetus | Gestational age | Age of mother |
|---|---|---|---|
| Cord#4 (Donor 1) | Female | 39 weeks | 30 |
| D0003 | Male | 39 weeks | 35 |
| E0004 | Female | 40 weeks | 34 |
| E0007 | Male | 39 weeks | 34 |

The accepted cord piece is placed in phosphate buffered saline (PBS) containing 100 IU/mL of penicillin and 100 µg/mL of streptomycin, stored at 4° C., and transported to the Midwest Stem Cell Therapy Center (MSCTC) for processing. The umbilical cord piece is maintained at 4° C. until processing, which must occur within 24 hours of receipt.

WJMSCs are explanted and isolated from the umbilical cord piece following tissue processing which includes the following steps: 1) washing the cord in sterile PBS supplemented with 400 IU/mL of penicillin and 400 µg/mL of streptomycin; 2) removal of the 2 arteries and 1 vein and additional washing to remove traces of unwanted blood cell contaminants; 3) preparing the cord fragments for explantation of the WJMSCs in cell culture dishes containing xeno-free, serum-free media; and 4) expansion of WJMSCs.

Process Flow Diagram.

Figure 9:
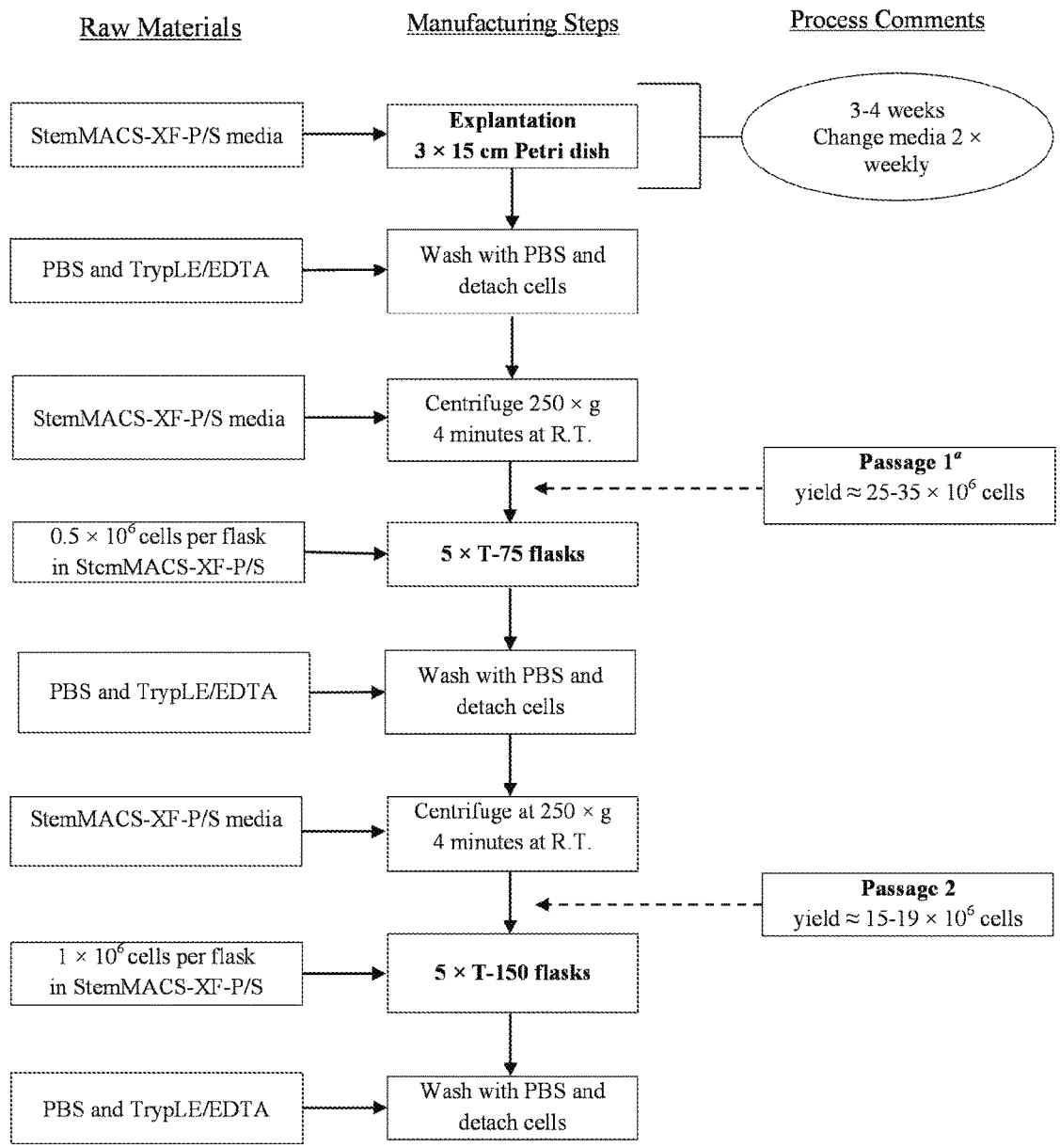
FIG. 9 is a flow diagram showing the explantation, expansion, formulation, and cryopreservation steps used for producing MSCTC-0010, Suspension for Infusion.
Figure 10:
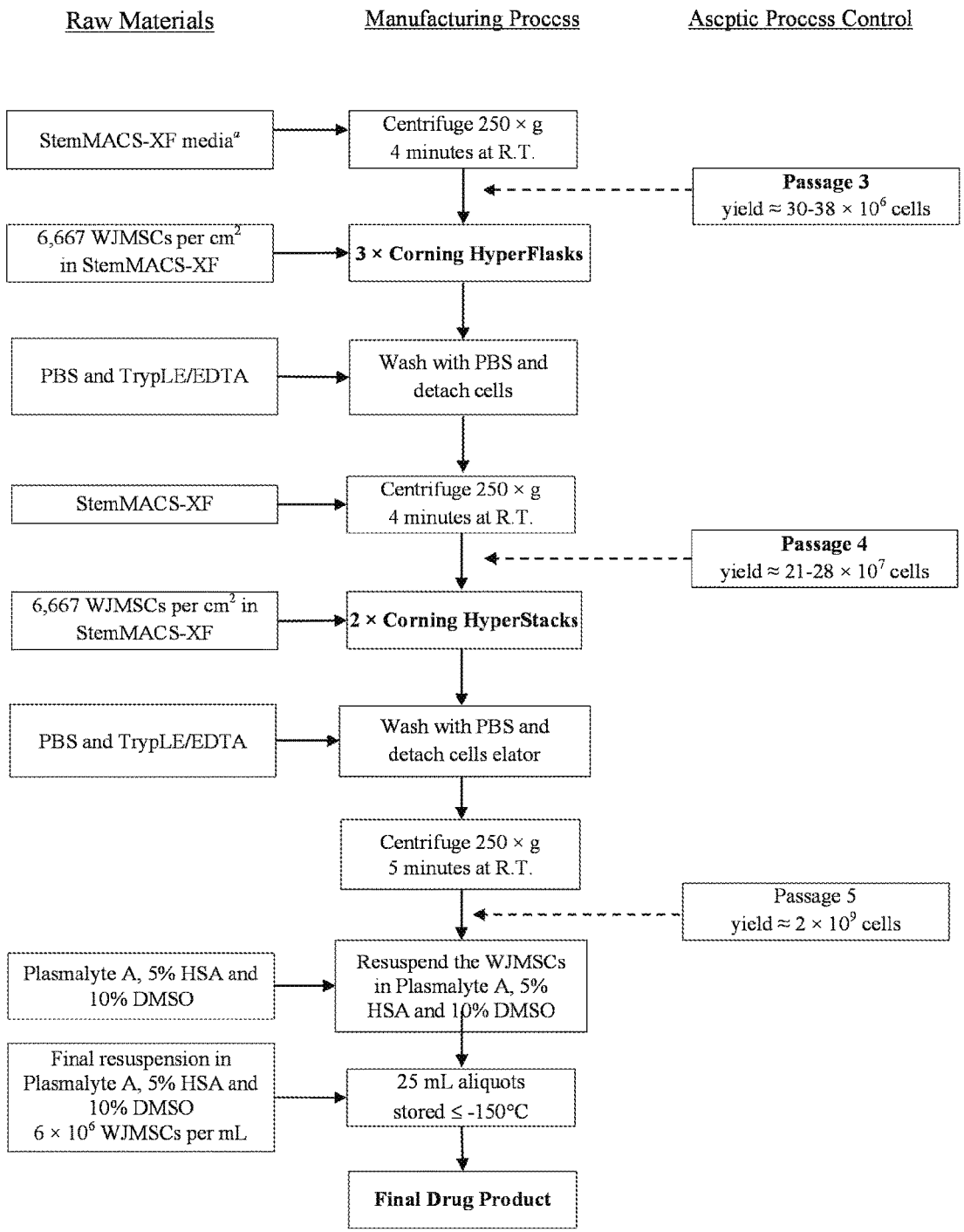
FIG. 10 is a flow diagram showing the explantation, expansion, formulation, and cryopreservation steps used for producing MSCTC-0010, Suspension for Infusion.

The process flow diagrams shown in FIG. 9 and FIG. 10 depict the explantation, expansion, formulation, and cryopreservation steps used for producing MSCTC-0010, Suspension for Infusion.

Explantation. To isolate WJMSCs from donated umbilical cord, the cord is placed inside a petri dish in a class II biosafety cabinet located within an aseptic suite of the MSCTC manufacturing area. The cord pieces are thoroughly washed in fresh, sterile PBS, supplemented with 400 IU/mL of penicillin and 400 µg/mL of streptomycin and then cut into approximately 4×5 cm-long pieces to facilitate the removal of the vessels within the umbilical cord. The 2 arteries and 1 vein are removed by cutting each piece of umbilical cord longitudinally to open the piece up and provide easy access to the vessels. Each vessel is removed and discarded using sterilized forceps and surgical scissors. Following vessel removal from each piece of cord, they are again washed with sterile PBS, supplemented with 100 IU/mL of penicillin and 100 µg/mL of streptomycin to insure removal of unwanted blood cell contaminants. Once each umbilical cord piece has had vessels removed and has been thoroughly washed to remove any visible signs of blood contamination, the remaining components of the umbilical cord are placed in a sterile petri dish containing 30 mL StemMACS™ MSC Expansion Media XF (StemMACS™-XF), and 100 IU/mL of penicillin, and 100 µg/mL of streptomycin (P/S). The pieces are minced with sterile scissors into 2- to 3-mm fragments. All cord fragments are then approximately equally distributed in 3-4×15-cm diameter sterile petri dishes covered with StemMACS™-XF+P/S media and incubated at 5% $CO_2$, 37° C. for approximately 3 to 4 weeks to allow cells of interest to migrate out of the tissue and attach to the petri dish. During this explantation period, media is changed twice per week and each dish monitored for the presence of WJMSCs.

Expansion—Passage 1.

Following the explantation period, tissue pieces are removed and discarded and the adherent WJMSCs are allowed to expand to 80% to 90/confluency as determined visually using a microscope. At this point, the WJMSCs are washed with PBS once and treated with 50% TrypLE Select (TrypLE Select diluted in PBS) to release the WJMSCs from the petri dishes. TrypLE Select activity is inhibited with the addition of 10 mL StemMACS™-XF+P/S media. The recovered cells are counted to determine the number of WJMSCs and then collected by centrifugation at 250×g for 4 minutes at room temperature. The cell pellets are resuspended in 40 mL StemMACS™-XF+P/S media. These recovered WJMSCs are designated as passage 1 and are considered the primary cell population.

Passage 2—

Cells ($2.5 \times 10^6$) from passage 1 are used to seed 5 T-75 flasks at $5 \times 10^5$ cells per flask in a total of 10 mL of StemMACS™-XF+P/S media. These cultures are maintained by replacing the StemMACS™-XF+P/S media twice weekly. The remaining cells from passage 1 ($22.5\text{-}32.5 \times 10^6$ WJMSCs) are centrifuged and resuspended in Plasmalyte A, 5% HSA and 10% DMSO aliquoted into cryovials and then frozen and stored at ≤−150° C. At approximately 80% visual confluency via microscopy, the WJMSCs are washed with PBS once and treated with 50% TrypLE Select (TrypLE Select diluted in PBS) to release the WJMSCs from the T-75 flasks. TrypLE Select activity is inhibited with the addition of 5 mL StemMACS™-XF+P/S media and the recovered cells are counted to determine the number of WJMSCs. The cells are then collected by centrifugation at 250×g for 4 minutes at room temperature and the cell pellets are resuspended in 40 mL StemMACS™-XF+P/S media. These recovered WJMSCs are designated as passage 2.

Passage 3—

Cells ($5 \times 10^6$) from passage 2 are used to seed 5×T-150 flasks at $1 \times 10^6$ cells per flask in a total of 20 mL StemMACS™-XF+P/S. These cultures are maintained by replacing the StemMACS™-XF+P/S media twice weekly until harvest. The remaining cells from passage 2 (approximately $10$-$14 \times 10^6$ WJMSCs) are centrifuged and resuspended in Plasmalyte A, 5% HSA and 10% DMSO, aliquoted into cryovials and then frozen and stored at $\leq -150°$ C. At approximately 80% visual confluency via microscopy, adherent WJMSCs are washed with PBS once and each flask treated with 50% TrypLE Select (TrypLE Select diluted in PBS) to release the WJMSCs from the T-150 flasks. TrypLE Select activity is then inhibited with the addition of 10 mL StemMACS™-XF media to each flask. The recovered cells are counted to determine the number of available WJMSCs and then collected by centrifugation at 250×g for 4 minutes at room temperature. The cell pellets are resuspended in StemMACS™-XF media as passage 3 cells and are used to seed 3 Corning HyperFlask units which have 1720 cm² of surface area, each. The HyperFlasks, prewarmed at 37° C., are each seeded at approximately $11.5 \times 10^6$ cells for a total of $34.5 \times 10^6$ cells. These cultures are incubated at 5% $CO_2$, 37° C. for 4 to 5 days to allow cells to attach to the unit and expand. The remaining cells (approximately $0$-$3.5 \times 10^6$ WJMSCs) from passage 3 are centrifuged and resuspended in Plasmalyte A, 5% HSA and 10% DMSO, aliquoted into cryovials and then frozen and stored at $\leq -150°$ C.

Passage 4—

At approximately 80% visual confluency via microscopy, media is removed from the HyperFlask, the adherent WJMSCs washed with PBS once and then treated with 50% TrypLE Select (TrypLE Select diluted in PBS) to release the WJMSCs from the HyperFlasks. TrypLE Select activity is inhibited with the addition of 100 mL StemMACS™-XF media into each HyperFlask. The TrypLE Select/Media mixture is then removed from each HyperFlask and pooled. Each flask is washed with 100 mL PBS to assure recovery of the maximum number of cells and the PBS washes are added to the TrypLE Select/Media pool and the entire volume mixed with gentle agitation at room temperature for approximately 30 seconds.

Recovery.

The recovered cells are counted to determine the number of available WJMSCs to be centrifuged at 250×g for 4 minutes at room temperature to seed 2 Corning HYPERStacks (target is $240 \times 10^6$ WJMSCs). The supernatant is removed and the cell pellets are resuspended in 200 mL StemMACS™-XF media. Two Corning HYPERStacks each of which has 18,000 cm² of surface area (36-layers), are prewarmed to 37° C. and seeded at approximately $120 \cdot 10^6$ cells each. These cultures are incubated at 5% $CO_2$, 37° C. for 5 days to allow cells to attach to the unit and expand. The remaining cells from passage 4 (approximately $0$-$40 \times 10^6$ WJMSCs) are centrifuged, resuspended in Plasmalyte A, 5% HSA and 10% DMSO, aliquoted into cryovials and then frozen and stored at $\leq -150°$ C.

Passage 5—

On day 5, media is removed from the 2 HYPERStack units, the adherent WJMSCs washed with 1000 ml PBS once and then treated with 50% TrypLE Select (TrypLE Select diluted in PBS) and StemMACS™-XF media is added to each of the HyperFlasks. The TrypLE Select/Media mixture is then removed from each HyperFlask and each flask is washed with 1000 ml PBS to recover the maximum number of cells. The PBS wash is added to the TrypLE Select/Media mixture and the entire volume pooled and mixed with gentle agitation for approximately 30 seconds.

Formulation.

The recovered cells are counted and collected by centrifugation at 500×g for 4 minutes at room temperature. The supernatant is removed and the cell pellets are resuspended at a concentration of $6 \times 10^6$ WJMSCs/mL in 70% Plasmalyte A, 5% HSA and 10% DMSO (v/v) and all resuspended pellets are pooled together and mixed with gentle agitation.

Cryopreservation.

The cell suspension is manually filled into CryoStore™ bags to produce 25-mL aliquots of MSCTC-0010, Suspension for Infusion ($150 \times 10^6$ WJMSCs/unit). The product is put through an initial freezing process using a controlled rate freezer. Once the cycle is complete, the product is transferred into long-term storage at $\leq -150°$ C.

Typical Yield.

The manufacturing scale for the phase 1 clinical study produces approximately $2 \times 10^9$ WJMSCs per batch. To produce this level of WJMSCs/batch, approximately $2.5 \times 10^6$ WJMSCs (8% to 9% of the WJMSCs recovered at P1) are used to start the expansion effort. Each level of expansion increases the WJMSCs population approximately 6-fold resulting in an overall expansion of 1300-fold from P1 to P5.

As described only a portion of the cells from passages 1 through 4 are utilized to produce the final cell product due to surface area limitations of the process developed to date. WJMSCs not utilized as phase clinical supplies are frozen for future research as needed.

| Process Controls | | |
|---|---|---|
| Step | Test | Acceptance Criteria |
| Explantation Expansion | Visual check | Plastic adherent, fibroblast like morphology |
| Passage 1 | Cell count | $\geq 2.5 \times 10^6$ |
| Passage 2 | Cell count | $\geq 5 \times 10^6$ |
| Passage 3 | Cell count | $\geq 34.4 \times 10^6$ |
| Passage 4 | Cell count | $\geq 240 \times 10^6$ |

Example 10: Grip Strength Test and Lifespan

Method: The stimulated hMSCs were applied to SOD1$^{G93A}$ mice by intrathecal injection ($1 \times 10^6$ cells, 1 million cells per injection in 50 µl DMEM/F12) as lumbar puncture at the vertebra L4/5 level and by intramuscular injection ($0.5 \times 10^6$ cells per injection in 50 µl DMEM/F12, two injections per muscle) into hind limb gastrocnemius muscles. Behavioral testing was performed 21 days following injection.

Grip Strength:

Grip strength of four limbs combined was measured with an Animal Grip Strength System (San Diego Instruments, San Diego, Calif.). The system utilizes a mesh wire grids, which the animal can grab with the four paws. The amount of strength is measured by force gauges attached to the mesh wire grids. Grip strength is recorded as the maximum amount of force, which the animal is able to exert while holding on to the grip. Triplicate determinations are averaged and data are presented as gram force.

Figure 11:
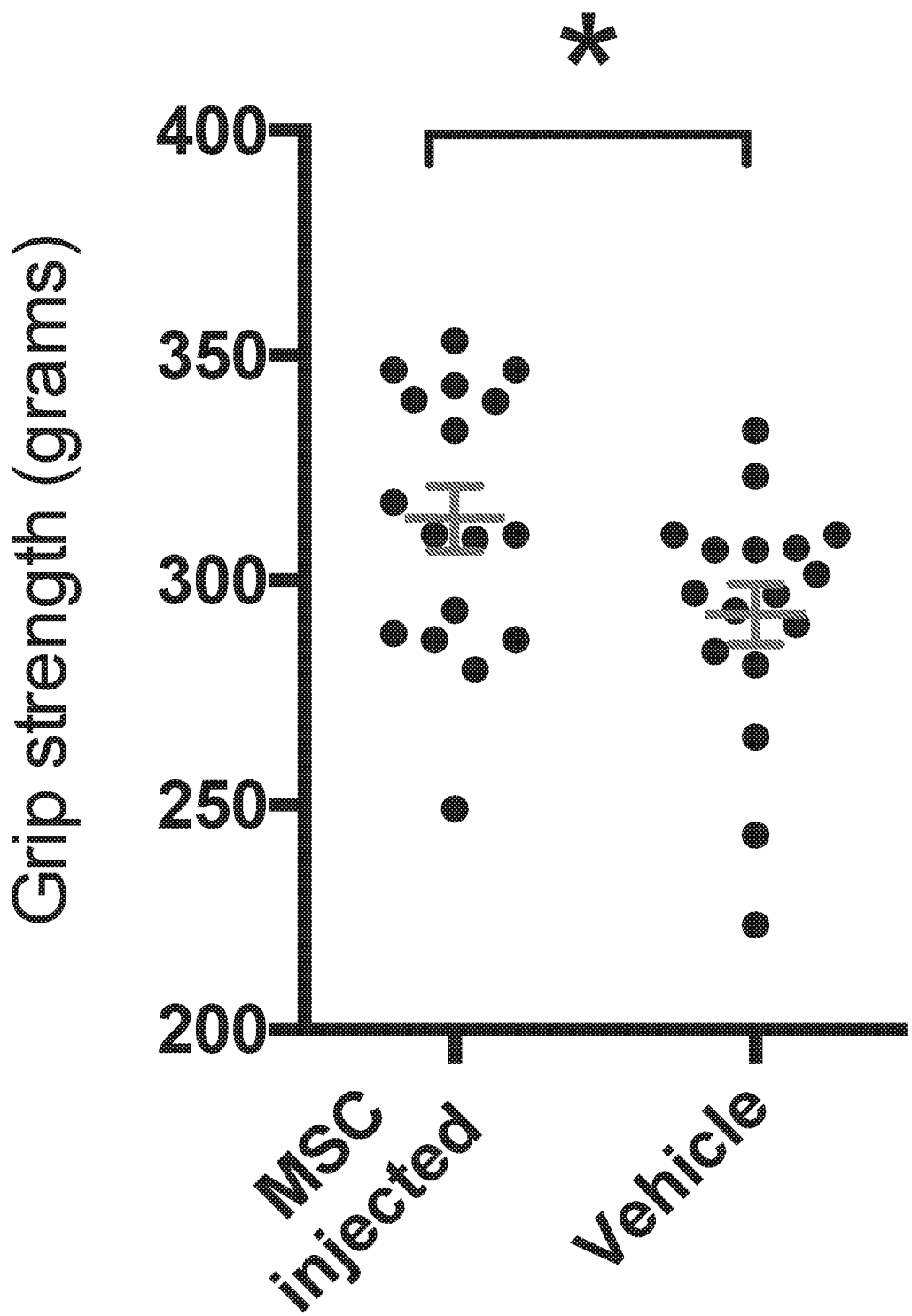
FIG. 11 is a graph showing average grip strength of SOD1$^{G93A}$ mice injected with stimulated human mesenchymal stem cells (hMSCs, 313.7 grams, left side graph) and SOD1$^{G93A}$ mice injected with vehicle (292.4 grams, right side graph).

Results:

The average grip strength force was stronger for SOD1$^{G93A}$ mice injected with stimulated human mesenchymal stem cells (hMSCs, 313.7 grams, FIG. 11, left side graph) compared to the SOD1$^{G93A}$ mice injected with vehicle (292.4 grams, FIG. 11, right side graph). The difference was statistically significant by unpaired t-test ($p<0.05$, n=17 animals each group). These results suggest that injection of stimulated hMSC has beneficial effect for neuromuscular function of the ALS model animal, SOD1G93A mice.

Hind Limb Stretching Phenotype and Lifespan:

Hind limb stretching phenotype and lifespan were monitored daily by a blinded observer using the neurological scoring system described by Leitner et al. (Leitner, M., Menzies, S., and Lutz, C. (2009). Working with ALS mice, guidelines for preclinical testing & colony management. PRIZE4LIFE, The Jackson Laboratory, 1-28). The hind limb stretching phenotype was recorded when tail hang of mice caused collapse or partial collapse or trembling of hind limbs (neurological score one). Neurological score four was recorded when mice cannot right itself within 30 seconds from either side. For survival assays, the end stage was defined as the age at which mice showed neurological score four.

Figure 12:
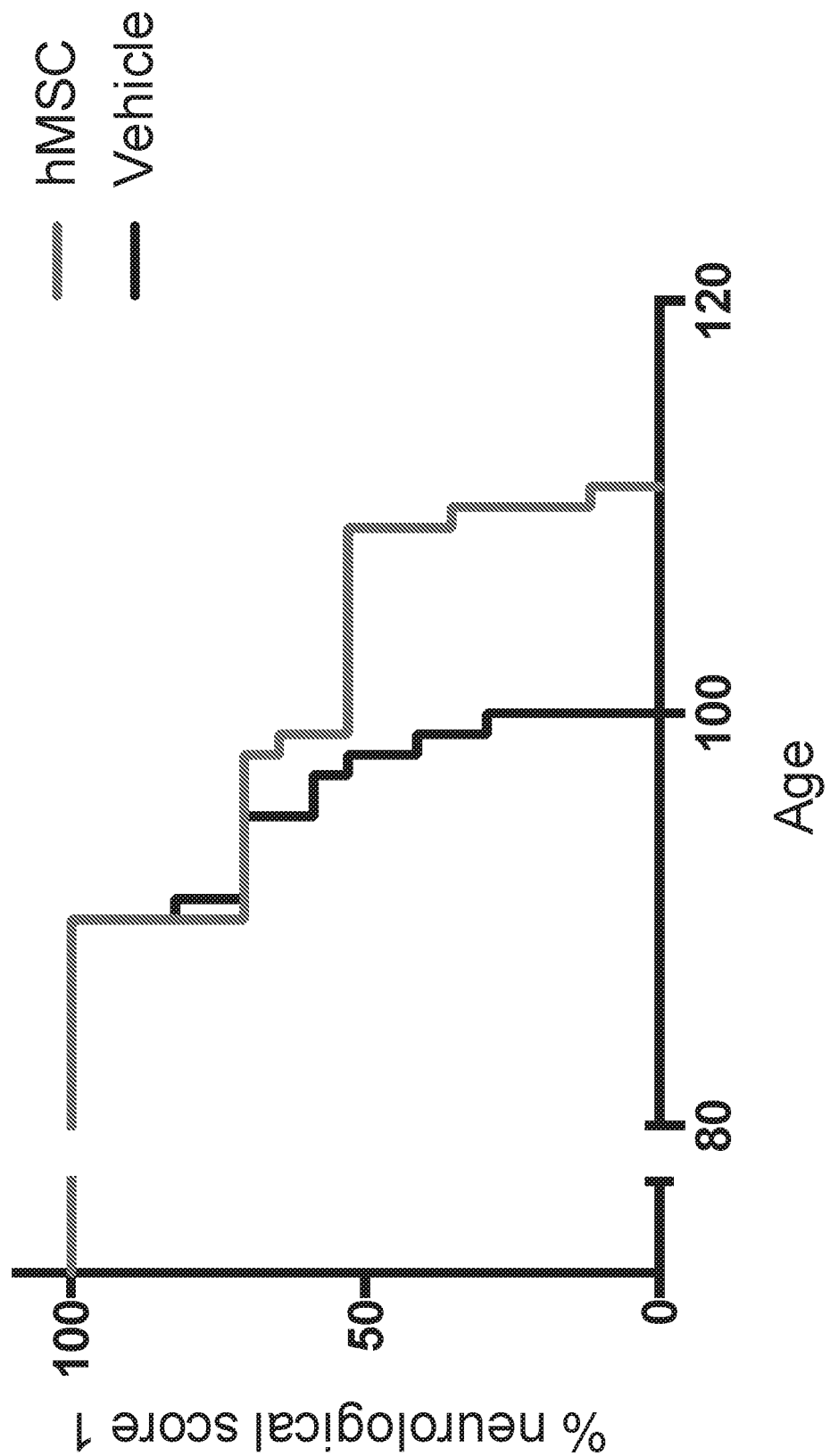
FIG. 12 is a graph showing the hind limb stretch phenotype for SOD1$^{G93A}$ mice injected with stimulated hMSCs (age 109 days, red line) and SOD1$^{G93A}$ mice injected with vehicle (age 98 days, black line).

Results:

As shown in FIG. 12, the hind limb stretch phenotype was delayed for SOD1$^{G93A}$ mice injected with stimulated human mesenchymal stem cells (age 109 days, red line) compared to the SOD1$^{G93A}$ mice injected with vehicle (age 98 days, black line). The difference was statistically significant by Log-rank (Mantel-Cox) test ($p=0.0091$, n=17 animals each group).

Figure 13:
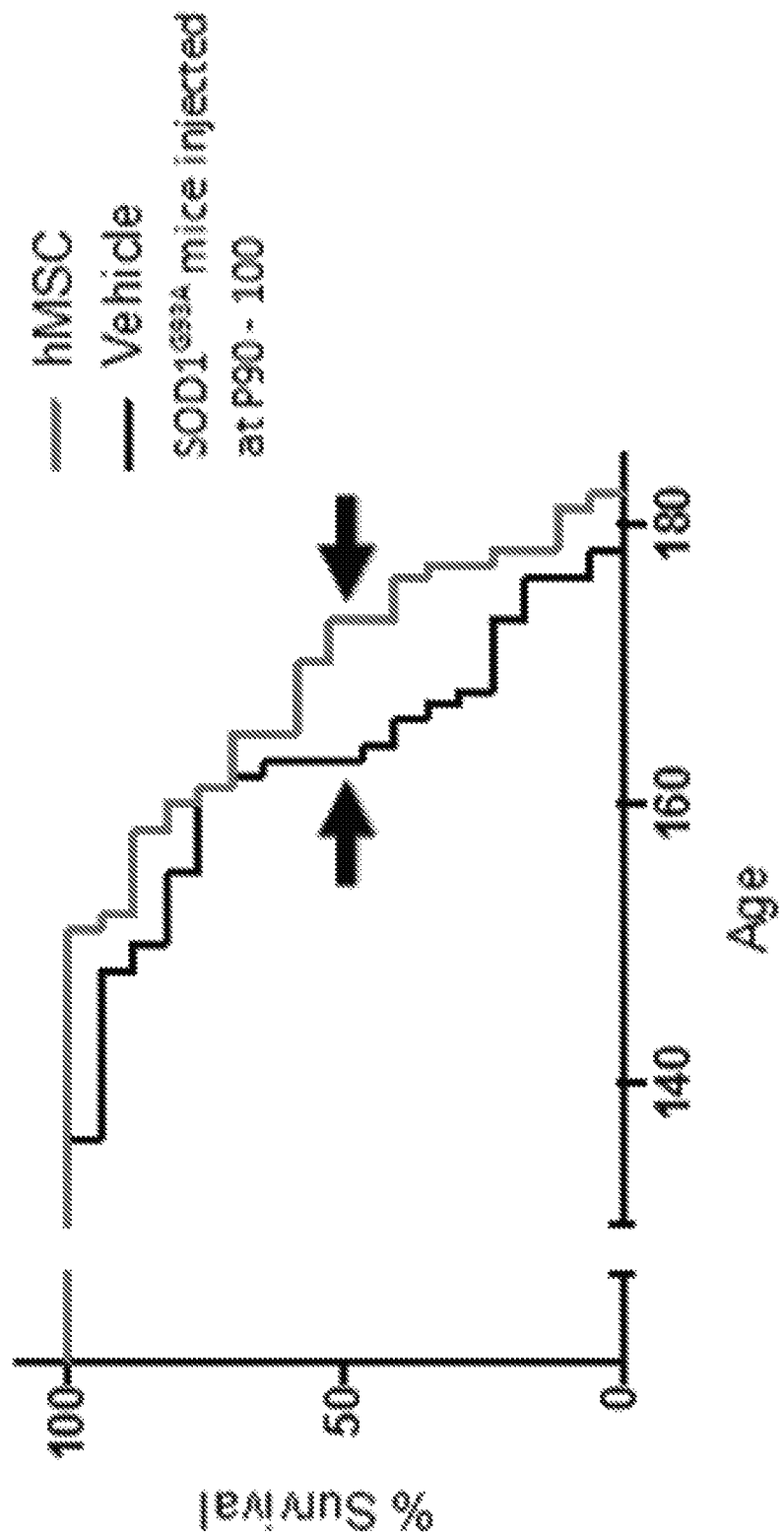
FIG. 13 is a graph showing lifespan for SOD1$^{G93A}$ mice injected with stimulated hMSCs (age 173 days, red line) and SOD1$^{G93A}$ mice injected with vehicle (age 163 days, black line).

As shown in FIG. 13, the lifespan was extended for SOD1$^{G93A}$ mice injected with stimulated human mesenchymal stem cells (age 173 days, red line) compared to the SOD1$^{G93A}$ mice injected with vehicle (age 163 days, black line). The difference was statistically significant by Log-rank (Mantel-Cox) test ($p=0.0484$, n=17 animals each group). These results suggest that injection of stimulated hMSC has beneficial effect for delaying the ALS symptom of the ALS model animal, SOD1$^{G93A}$ mice.

Example 11: Cd140b Expression

RNA Isolation—

Trizol/Phaselock Gel: Frozen umbilical stem cells were submersed in 1 ml Trizol (Invitrogen) and homogenized using PowerGen 35 homogenizer with a micro tip (Fisher Scientific). Homogenized tissue lysate is added to a 1.5 ml PhaseLock Gel Heavy tube (ThermoFisher) for separation of the aqueous and organic phases by microcentrifugation. Aqueous phase was adjusted with 2-Propanol and the RNA is precipitated at 13,000 rpm at 4 C. RNA pellet is washed two times with 1 ml of 4 C 80% ethanol with 5 minute centrifugation at 4 C for each wash. Pellets were air dried for 15 minutes and resuspended in 100 ul nuclease free H2O. Purified RNA was assayed for concentration using the Nanodrop and quality control was performed using an Agilent Bioanalyzer run using a RNA6000 Nano 11 LabChip (Agilent Technologies 5067-1511).

NuGEN Universal Plus mRNA-Seq:

The Stranded mRNA-Seq was performed using the Illumina NovaSeq 6000 Sequencing System at the University of Kansas Medical Center—Genomics Core (Kansas City, Kans.).

Total RNA (1 ug) was used to initiate the library preparation protocol. The total RNA fraction was processed by oligo dT bead capture of mRNA, mRNA fragmentation, reverse transcription into cDNA, end repair of cDNA, ligation with the appropriate Unique Dual index adaptors (UDI), strand selection and 16 cycles of library amplification by PCR using the Universal Plus mRNA-seq library preparation protocol (NuGEN 0508-08, 0508-32).

Library validation was performed using the DNA 1000 kit II (Agilent Technologies 5067-1504) on the Agilent Bioanalyzer 2100. Following NanoDrop assay (ThermoFisher), each library is diluted to 4 nM and a final library quantification is conducted, in triplicate, using the Roche Lightcycler96 with FastStart Essential DNA Green Master (Roche 06402712001) and KAPA Library Quant (Illumina) DNA Standards 1-6 (KAPA Biosystems KK4903). Using the qPCR results, RNA-Seq libraries were adjusted to 2 nM concentration and pooled for multiplexed sequencing.

Pooled libraries were denatured with NaOH (0.1N final) and diluted to 425 pM concentration with HT1 buffer (Illumina PE402-4002) followed by automated onboard clonal clustering of the S1 patterned flow cell using the NovaSeq 6000 Reagent kit 200 cycle (Illumina 20012864). The clustered flow cell was sequenced on the Illumina NovaSeq 6000 Sequencing System using a 101×9×9×101 paired end sequencing strategy. Following collection, sequence data is converted from .bcl file format to fastQ files and de-multiplexed into individual sequences for further downstream analysis.

RNA-Seq data analysis: RNA-Sequencing was performed at a strand specific 100 cycle paired-end resolution, in an Illumina NovaSeq sequencing machine (Illumina, San Diego, Calif.). Three matched paired biological replicate samples, each from Passage 1 and Passage 5 were analyzed for differential gene expression. The six samples were multiplexed in a NovaSeq-S1 flow-cell, resulting between 31 and 37.5 million reads per sample. The read quality was assessed using the FastQC software 1. On average, the per sequence quality score measured in the Phred quality scale was above 32 for all the samples. The reads were mapped to the human genome (GRCh38.rel92) using the STAR software, version 2.3.1z2. Around 99% of the sequenced reads mapped to the reference genome in all six samples, resulting between 31 and 37.4 million mapped reads per sample, of which on average 95% were uniquely mapped reads. Transcript abundance estimates were calculated using the RSEM3 (version 1.3.0) software. Expression normalization and differential gene expression calculations were performed in edgeR4 (release 2.14) to identify statistically significant differentially expressed genes. EdgeR employs a negative binomial generalized linear model (NB-GLM) for statistical calculations. The edgeR package implements advance empirical Bayes methods to estimate gene-specific biological variation under minimal levels of biological replication. The RNA composition in each sample was normalized in edgeR using the trimmed mean of M-values (TMM) method. The significance p-values were adjusted for multiple hypotheses testing by the Benjamini and Hochberg method5 establishing a false discovery rate (FDR) for each gene.

Results: As shown in FIG. 14, a high expression of cd140b at passage 5 was detected in three MSC lines obtained from three different donors (D0002, D0003, E0007).

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses, as well as the following claims:

Clause 1. An isolated non-genetically modified human cell activated ex vivo from a mesenchymal stem cell (MSC) under conditions such that the isolated non-genetically modified human cell secretes laminin β2 at a level that is greater than the basal secretion level of laminin β2 by the MSC.

Clause 2. The isolated human cell of clause 1, wherein MSC is obtained from Wharton's jelly from an umbilical cord.

Clause 3. The isolated human cell of either clause 1 or clause 2, wherein the MSC is CD140b positive.

Clause 4. The isolated human cell of any of clauses 1-3, wherein the cell is activated in a cell culture composition comprising cell culture media and Insulin-like growth factor 1 (IGF-1)

Clause 5. The isolated human cell of clause 4, wherein the cell culture composition further comprises one or more additional growth factors selected from Fibroblast Growth Factor (FGF) and Platelet-derived Growth Factor (PDGF).

Clause 6. The isolated human cell of either clause 4 or clause 5, wherein the cell culture composition further comprises Heregulin β1.

Clause 7. The isolated human cell of any of clauses 4-6, wherein the cell culture media is DMEM-F12 containing L-glutamine.

Clause 8. The isolated human cell of any of clauses 4-7, wherein the cell culture composition further comprises dibutryl cAMP.

Clause 9. The isolated human cell of any of clauses 4-8, wherein the cell culture composition further comprises 3-isobutyl-1-methylxanthine (IBMX).

Clause 10. The isolated human cell of any of clauses 1-9, wherein the isolated non-genetically modified human cell further secretes one or more of glial cell-derived neurotrophic factor (GDNF), brain-derived neurotrophic factor (BDNF), and vascular endothelial growth factor (VEGF) at a level that is greater than the basal secretion level of GDNF, BDNF, or VEGF by the MSC.

Clause 11. The isolated human cell of any of clauses 1-10, wherein the isolated human cell enhances growth and/or survival of one or more motor nerve terminals at a neuromuscular junction upon exposure to the activated MSCs.

Clause 12. The isolated human cell of any of clauses 1-11, wherein the isolated human cell ameliorates denervation at a neuromuscular junction caused by Amyotrophic Lateral Sclerosis (ALS).

Clause 13. A method of treating a disease for which administration of neurotrophic factors is beneficial in a subject in need thereof, comprising administering to the subject the isolated human cell of any of clauses 1-12.

Clause 14. The method of clause 13, wherein the diseases is ALS.

Clause 15. A method for producing a cell from a mesenchymal stem cell (MSC), such that the cell secretes laminin β2 at a level that is greater than the basal secretion level of laminin β2 by the MSC, the method comprising exposing the MSC to a cell culture composition comprising cell culture media and Insulin-like growth factor 1 (IGF-1).

Clause 16. The method of clause 15, wherein the MSC is obtained from Wharton's jelly from an umbilical cord.

Clause 17. The method of either clause 15 or clause 16, wherein the MSC is CD140b positive.

Clause 18. The method of any of clauses 15-17, wherein the cell culture composition further comprises one or more additional growth factors selected from Fibroblast Growth Factor (FGF) and Platelet-derived Growth Factor (PDGF).

Clause 19. The method of any of clauses 15-18, wherein the cell culture composition further comprises Heregulin β1.

Clause 20. The method of any of clauses 15-19, wherein the cell culture media is DMEM-F12 containing L-glutamine.

Clause 21. The method of any of clauses 15-20, wherein the cell culture composition further comprises dibutryl cAMP.

Clause 22. The method of any of clauses 15-21, wherein the cell culture composition further comprises 3-isobutyl-1-methylxanthine (IBMX).

Clause 23. The method of any of clauses 15-22, wherein the cell further secretes one or more of glial cell-derived neurotrophic factor (GDNF), brain-derived neurotrophic factor (BDNF), and vascular endothelial growth factor (VEGF) at a level that is greater than the basal secretion level of GDNF, BDNF, or VEGF by the MSC.

Clause 24. The method of any of clauses 15-23, wherein the cell enhances growth and/or survival of one or more motor nerve terminals at a neuromuscular junction upon exposure to the cell.

Clause 25. The method of any of clauses 15-24, wherein the cell ameliorates denervation at a neuromuscular junction caused by Amyotrophic Lateral Sclerosis (ALS).

What is claimed is:

1. A method for producing a cell from a mesenchymal stem cell (MSC) obtained from Wharton's jelly from an umbilical cord, such that the cell secretes laminin β2 at a level that is greater than the basal secretion level of laminin β2 by the MSC, the method comprising:
    exposing the MSC to a cell culture composition comprising DMEM-F12 cell culture media containing L-glutamine, 3-isobutyl-1-methylxanthine (IBMX), dibutyryl cAMP, Fibroblast Growth Factor (FGF), Heregulin β1, Platelet-derived Growth Factor (PDGF), and Insulin-like growth factor 1 (IGF-1).

2. The method of claim 1, wherein the MSC is CD140b positive.

3. The method of claim 1, wherein the cell culture composition comprises Fibroblast Growth Factor (FGF) at a concentration of 20 ng/mL and Platelet-derived Growth Factor (PDGF) at a concentration of 5 ng/mL.

4. The method of claim 1, wherein the cell culture composition comprises Heregulin β1 at a concentration of 50 ng/mL.

5. The method of claim 1, wherein the DMEM-F12 cell culture media contains 2.5 mM L-glutamine.

6. The method of claim 1, wherein the cell culture composition comprises dibutyryl cAMP at a concentration of 1 mM.

7. The method of claim 1, wherein the cell culture composition comprises 3-isobutyl-1-methylxanthine (IBMX) at a concentration of 0.5 mM.

8. The method of claim 1, wherein the cell further secretes one or more of glial cell-derived neurotrophic factor (GDNF), brain-derived neurotrophic factor (BDNF), and vascular endothelial growth factor (VEGF) at a level that is greater than the basal secretion level of GDNF, BDNF, or VEGF by the MSC.

9. The method of claim 1, wherein the cell enhances growth and/or survival of one or more motor nerve terminals at a neuromuscular junction upon exposure to the cell.

10. The method of claim 1, wherein the cell ameliorates denervation at a neuromuscular junction caused by Amyotrophic Lateral Sclerosis (ALS).

11. A method of treating a disease for which administration of neurotrophic factors is beneficial in a subject in need thereof, comprising administering to the subject an isolated non-genetically modified human cell activated ex vivo from a mesenchymal stem cell (MSC) obtained from Wharton's jelly from an umbilical cord under conditions such that the isolated non-genetically modified human cell secretes laminin β2 at a level that is greater than the basal secretion level of laminin β2 by the MSC, wherein the cell is activated in a cell culture composition comprising DMEM-F12 cell culture media containing L-glutamine, 3-isobutyl-1-methylxanthine (IBMX), dibutyryl cAMP, Fibroblast Growth Factor (FGF), Heregulin β1, Platelet-derived Growth Factor (PDGF), and Insulin-like growth factor 1 (IGF-1).

12. The method of claim 11, wherein the diseases is ALS.

* * * * *